United States Patent
Rossi et al.

(10) Patent No.: US 11,357,796 B2
(45) Date of Patent: Jun. 14, 2022

(54) TREATMENT USING CHIMERIC RECEPTOR T CELLS INCORPORATING OPTIMIZED POLYFUNCTIONAL T CELLS

(71) Applicant: Kite Pharma, Inc., Santa Monica, CA (US)

(72) Inventors: John M. Rossi, Santa Monica, CA (US); Adrian I. Bot, Santa Monica, CA (US)

(73) Assignee: KITE PHARMA, INC., Santa Monica, CA (US)

( * ) Notice: Subject to any disclaimer, the term of this patent is extended or adjusted under 35 U.S.C. 154(b) by 106 days.

(21) Appl. No.: 15/944,484

(22) Filed: Apr. 3, 2018

(65) Prior Publication Data
US 2018/0296601 A1 Oct. 18, 2018

Related U.S. Application Data

(60) Provisional application No. 62/481,003, filed on Apr. 3, 2017.

(51) Int. Cl.
| | |
|---|---|
| *A61K 35/17* | (2015.01) |
| *A61P 35/00* | (2006.01) |
| *C07K 16/28* | (2006.01) |
| *G01N 33/574* | (2006.01) |
| *G01N 33/68* | (2006.01) |
| *A61K 39/00* | (2006.01) |
| *G01N 33/50* | (2006.01) |

(52) U.S. Cl.
CPC .......... *A61K 35/17* (2013.01); *A61K 39/0011* (2013.01); *A61P 35/00* (2018.01); *C07K 16/2803* (2013.01); *G01N 33/5011* (2013.01); *G01N 33/574* (2013.01); *G01N 33/6893* (2013.01); *A61K 2039/5156* (2013.01); *A61K 2039/5158* (2013.01); *A61K 2039/572* (2013.01); *A61K 2039/70* (2013.01)

(58) Field of Classification Search
CPC ..... A61K 35/17; A61P 35/00; C07K 16/2803; G01N 33/5011; G01N 33/574; G01N 33/6893
USPC .......................................................... 435/325
See application file for complete search history.

(56) References Cited

U.S. PATENT DOCUMENTS

| | | | |
|---|---|---|---|
| 5,728,388 | A | 3/1998 | Terman |
| 5,827,642 | A | 10/1998 | Riddell et al. |
| 6,040,177 | A | 3/2000 | Riddell et al. |
| 6,319,494 | B1 | 11/2001 | Capon et al. |
| 6,797,514 | B2 | 9/2004 | Berenson et al. |
| 6,867,041 | B2 | 3/2005 | Berenson et al. |
| 6,905,874 | B2 | 6/2005 | Berenson et al. |
| 7,741,465 | B1 | 6/2010 | Eshhar et al. |
| 9,855,298 | B2 | 1/2018 | Bot et al. |
| 10,040,846 | B2 | 8/2018 | Frigault et al. |
| 2002/0006409 | A1 | 1/2002 | Wood |
| 2013/0287748 | A1 | 10/2013 | June et al. |
| 2014/0050708 | A1 | 2/2014 | Powell et al. |
| 2014/0099309 | A1 | 4/2014 | Powell et al. |
| 2014/0154228 | A1 | 6/2014 | Volk et al. |
| 2014/0227237 | A1 | 8/2014 | June et al. |
| 2015/0283178 | A1* | 10/2015 | June ........................ A61P 35/02 424/85.2 |

FOREIGN PATENT DOCUMENTS

| | | |
|---|---|---|
| JP | 2015-513399 A | 8/2013 |
| JP | 2015-513399 A | 5/2015 |
| KR | 10-2014-0127816 A | 11/2014 |
| WO | 2008/081035 A1 | 7/2008 |
| WO | 2012/079000 A1 | 6/2012 |
| WO | 2012/129514 A1 | 9/2012 |
| WO | 2013126712 A1 | 8/2013 |
| WO | 2016/191755 A1 | 12/2016 |
| WO | WO 2018/049418 A1 | 3/2018 |

OTHER PUBLICATIONS

Baron et al., "DNA demethylation in the human FOXP3 locus discriminates regulatory T cells from activated FOXP3(+) conventional T cells", Eur J Immunol, 37(9): 2378-2389 (2007).
Cheson et al., "Recommendations for initial evaluation, staging, and response assessment of Hodgkin and non-Hodgkin lymphoma: the Lugano classification", Journal of Clinical Oncology, 32(27): 3059-3067 (2014).
Cheson et al. "Revised response criteria for malignant lymphoma", Journal of Clinical Oncology, 25(5): 579-86 (2007).
Eshhar et al., "Tumor-specific T-bodies: towards clinical application", Cancer Immunol Immunotherapy, 45(3-4): 131-136 (1997).
Finney et al., "Chimeric receptors providing both primary and costimulatory signaling in T cells from a single gene product", Journal of Immunology, 161(6): 2791-2797 (1998).
Gross et al., "Therapeutic Potential of T Cell Chimeric Antigen Receptors (CARs) in Cancer Treatment: Counteracting Off-Tumor Toxicities for Safe CAR T Cell Therapy", Annu Rev Pharmacol. Toxicol., 56: 59-83 (2016).
Kalos et al., "T cells with chimeric antigen receptors have potent antitumor effects and can establish memory in patients with advanced leukemia", Sci. Transl. Med., 3(95): 95ra73 (2011).
Kochenderfer et al., "B-cell depletion and remissions of malignancy along with cytokine-associated toxicity in a clinical trial of anti-CD19 chimeric-antigen-receptor-transduced T cells", Blood, 119(12): 2709-20 (2012).

(Continued)

*Primary Examiner* — Yan Xiao
(74) *Attorney, Agent, or Firm* — Arrigo, Lee, Guttman & Mouta-Bellum LLP; Carla Mouta-Bellum

(57) ABSTRACT

The disclosure provides methods of treating a malignancy comprising administering an effective dose of a chimeric receptor (e.g., CAR or TCR) genetically modified T cell immunotherapy. Some aspects of the disclosure relate to methods of determining an effective dose of a T cell immunotherapy comprising polyfunctional T cells prior to administration to the patient.

16 Claims, 25 Drawing Sheets
Specification includes a Sequence Listing.

(56) References Cited

OTHER PUBLICATIONS

Kochenderfer et al., "Lymphoma remissions caused by anti-CD19 chimeric antigen receptor T cells are associated with high serum interleukin-15 levels", J Clin Oncol, 35(16): 1803-1813 (2017).
Krause et al., "Antigen-dependent CD28 Signaling Selectively Enhances Survival and Proliferation in Genetically Modified Activated Human Primary T Lymphocytes", J. Exp Med., 188(4): 619-626 (1998).
Ma et al., "Multifunctional T-cell analyses to study response and progression in adoptive cell transfer immunotherapy", Cancer Discov., 3(4): 418-29 (2013).
Porter et al., "Chimeric antigen receptor-modified T cells in chronic lymphoid leukemia", N. Engl. J. Med., 365(8): 725-33 (2011).
Song et al., "CD27 costimulation augments the survival and antitumor activity of redirected human T cells in vivo", Blood, 119(3): 696-706 (2012).
Alexander Muir Sutherland, "Technology for Single Cell Protein Analysis in Immunology and Cancer Prognostics" (2016) pp. 1-116, Ph.D. Thesis, California Institute of Technology.
Fraietta J. A. et al., "Identification of Functional Determinants of Response and Resistance to CD19 Chimeric Antigen Receptor (CAR) T-Cell Therapy of Chronic Lymphocytic Leukemia". Blood (2017), vol. 130: 3181, suppl. 1.
International Search Report dated Jun. 28, 2018 for PCT/US2018/025888 filed Apr. 3, 2018, and published as WQ2018/187332 with publication date Oct. 11. 2018.
Office Action dated Sep. 4, 2020 for Australian Patent Application No. 2018250148.
Original and English Translation of Office Action dated Jul. 26, 2020 in Israeli Patent Application No. 269629.
Office Action dated Jan. 5, 2021 for Japanese Patent Application No. 2019-553470, original and English Version.
Uchibori, R. (2016), "Adoptive Immuno-gene and Cell Therapy with CAR-redirected T Cells," History of Medicine (Igaku-no Ayumi), vol. 257(3), 239-243, English translation.
Notice of Preliminary Rejection in counterpart Korean Application No. 10-2019-7032119, dated Apr. 26, 2021.
English Translation of Preliminary Rejection in counterpart Korean Application No. 10-2019-7032119, dated May 3, 2021.
Office Action in counterpart Canadian Application No. 3,057,880 dated May 3, 2021.
Office Action in counterpart Japanese Application No. 2019-553470, dated Aug. 31, 2021 Original and English Translation, citing JP Patent Application No. 2015-513399A/US counterpart is U.S. Pat. No. 10,040,845, submitted herewith.
Notice of Acceptance in counterpart Australian Application No. 2018250148, dated Sep. 9, 2021.
Canadian Office Action dated Feb. 10, 2022 in connection with Canadian Application No. 3,057,880, 4 pages.
Korean Office Action dated Feb. 24, 2022 in connection with Korean Application No. 10-2019-7032119, 6 pages.
English language translation of Korean Office Action dated Feb. 24, 2022 in connection with Korean Application No. 10-2019-7032119, 7 pages.

* cited by examiner

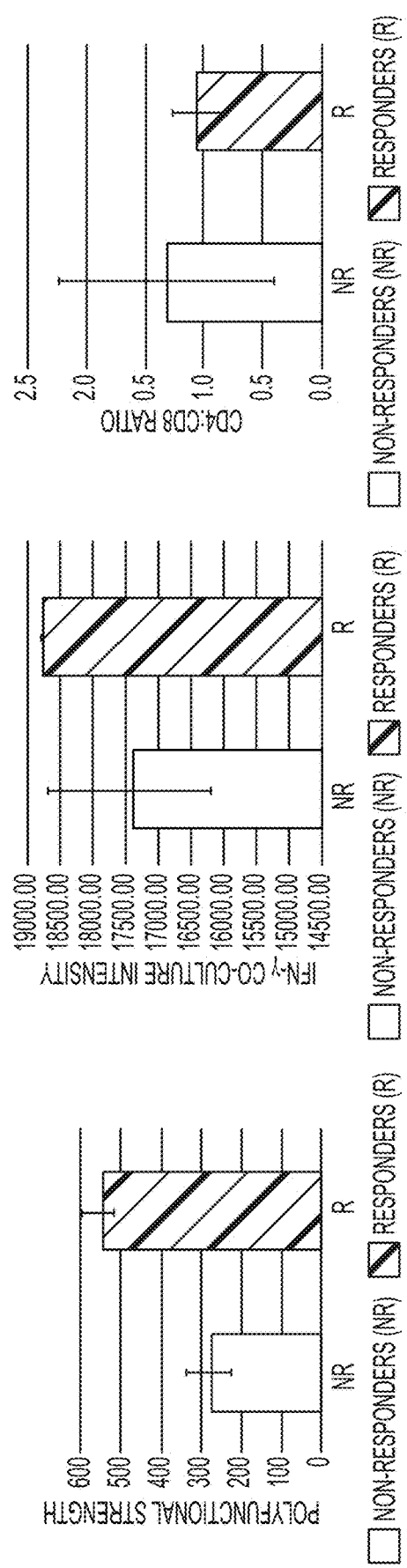

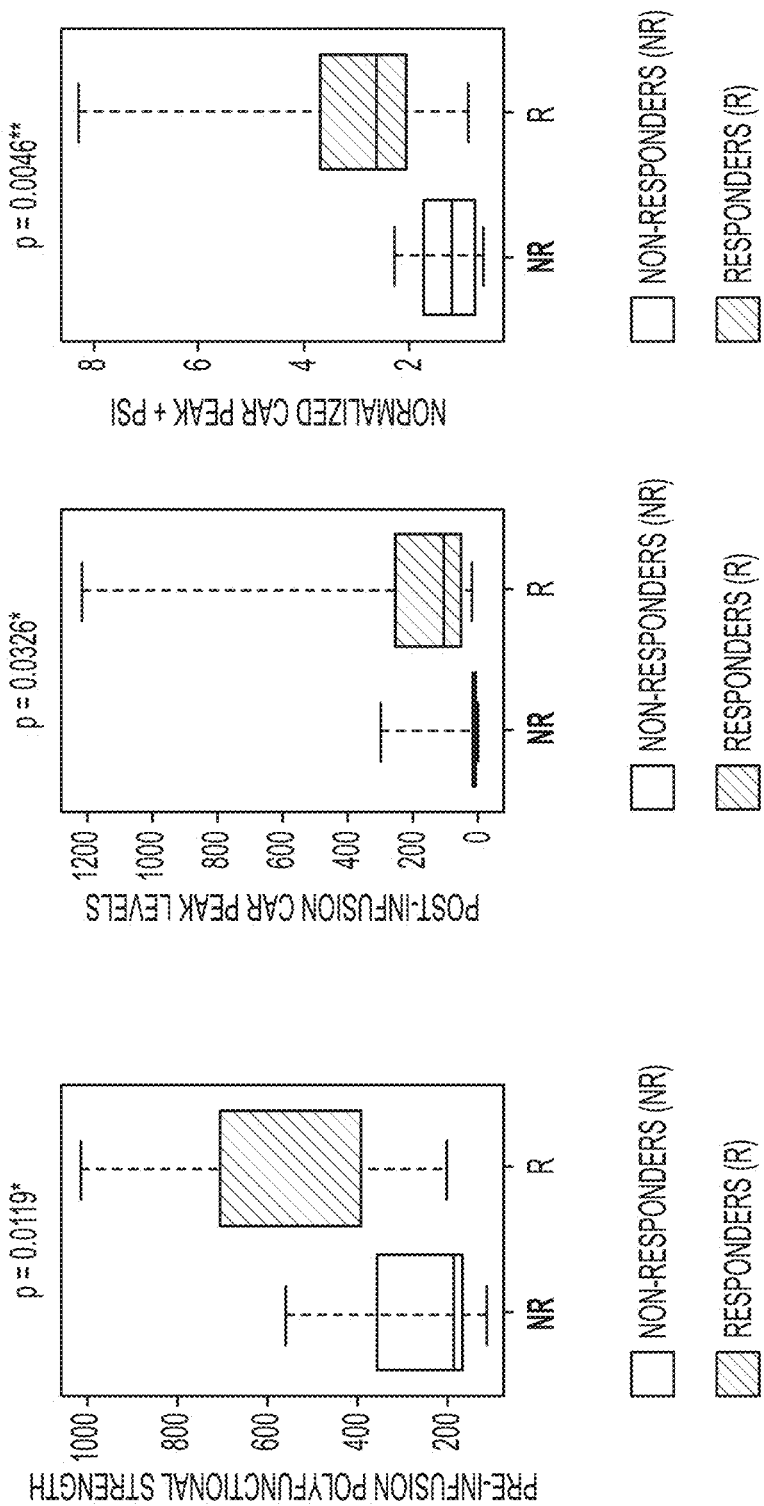

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: polypeptide linker

<400> SEQUENCE: 1

Gly Ser Thr Ser Gly Ser Gly Lys Pro Gly Ser Gly Glu Gly Ser Thr
1               5                   10                  15

Lys Gly

TREATMENT USING CHIMERIC RECEPTOR T CELLS INCORPORATING OPTIMIZED POLYFUNCTIONAL T CELLS

CROSS REFERENCE TO RELATED APPLICATIONS

This application claims priority to U.S. Provisional Application 62/481,003 filed Apr. 3, 2017, which is incorporated by reference in its entirety.

SEQUENCE LISTING

The instant application contains a Sequence Listing which has been submitted electronically in ASCII format and is hereby incorporated by reference in its entirety. Said ASCII copy, created on Apr. 3, 2018, is named KPI-019US1_ST25.txt and is 564 bytes in size.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

SUMMARY

A subset of CAR T cells, in pre-infusion product, comprising individual T cells capable of deploying multiple immune programs orchestrate CAR T cell potency. Polyfunctional profiles for both CD4+ and CD8+ T cells stimulated with CD19+ target cells are composed of select effector molecules (Granzyme B), stimulatory/immune modulating cytokines (IFNγ, IL-5), and chemokines (IL-8, MIP-1α). In contrast to CD8+ T cells, the CD4+ T cell subset also comprised IL-17A-secreting polyfunctional cells. The diversity and co-participation of CD4+ and CD8+ T cells to the polyfunctional T cell population is consistent with a CAR product with a CD28 co-stimulatory domain.

As described herein, clinical response and toxicities resulting from CAR T cell treatment are associated with the Polyfunctional Strength Index (PSI) of chimeric receptor T cells, or defined T cell subpopulations.

Described herein, is a novel product attribute for chimeric receptor T cells (e.g., CAR T cells or exogenous TCR cells), which is associated with T cell polyfunctionality, and correlated with clinical outcome. The polyfunctionality index combined with conditioning-driven IL-15—a cytokine with potent T cell proliferative capabilities—or CAR T cell expansion in vivo associates with clinical outcomes post-CAR T cell therapy.

Monitoring CAR T cell polyfunctionality is useful as a key product attribute, complementing other characteristics such as T cell proliferative capability. In some embodiments, polyfunctionality is at least determined by the status of T cells before manufacturing. In some embodiments, polyfunctionality and clinical outcome could be manipulated through optimizing the genetic programming of T cells, the manufacturing process, or dosing strategy.

The present disclosure relates to methods of treating a malignancy in a patient comprising administering to said patient an effective dose of a chimeric receptor, said method comprising obtaining a plurality of T cells, said T cells containing one or more chimeric antigen receptors, and administering a dose of said T cells wherein said dose comprises an effective amount of polyfunctional CAR T cells. The polyfunctional T cells comprise, e.g., CD8+ and CD4+ polyfunctional T cells.

The method further comprises obtaining the effective percentage of polyfunctional CAR T cells using a Polyfunctional Strength Index percentage to determine the desired dose. The Polyfunctional Strength Index comprises incorporating a determination of desired percent Polyfunctional T cells along with calculation of a pre-determined cytokine profile. The pre-determined cytokine profile comprises, for example, the measurement and selection of at least one of Granzyme B, IFN-gamma, MIP1α, Perforin, TNFa, TNFb, GMCSF, IL-2, IL-5, IL-7, IL-8, IL-9, IL-12, IL-15, IL-21, CCI-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4. In some embodiments, 20-25% of all product cells upon stimulation with CD19-expressing target cells were polyfunctional.

The chimeric receptor can be a chimeric antigen receptor (CAR) and/or a T cell receptor (TCR).

The disclosure further relates to methods of treating a malignancy in a patient comprising administering to said patient an effective dose of a chimeric receptor selected from the group consisting of chimeric antigen receptors and T cell receptors wherein said dose contains an effective percentage of polyfunctional CAR T cells. The invention further relates to a method of reducing undesired side effects in a chimeric receptor treatment comprising modulating the percentage of polyfunctional CAR T cells, as well as methods of increasing potency of a chimeric receptor treatment comprising modulating the percentage of polyfunctional CAR T cells.

In one aspect, the present disclosure provides a method of treating a malignancy in a patient comprising: (a) obtaining a plurality of T cells comprising one or more chimeric receptors; and administering an effective dose of the T cells to the patient, wherein the effective dose comprises a pre-determined amount of polyfunctional T cells.

In some embodiments, the predetermined amount of polyfunctional T cells is greater than 15%, greater than 20%, greater than 20%, greater than 25%, greater than 30% polyfunctional T cells.

In some embodiments, the predetermined amount of polyfunctional T cells is determined using the Polyfunctional Strength Index (PSI).

In some embodiments, the Polyfunctional Strength Index (PSI) is calculated by multiplying the percentage of polyfunctional cells by the sum of the mean intensity of the proteins secreted by the polyfunctional cells.

In some embodiments, the Polyfunctional Strength Index (PSI) is calculated by multiplying the percentage of polyfunctional cells by the sum of the mean fluorescence intensity of the proteins secreted by the polyfunctional cells. In some embodiments, the Polyfunctional Strength Index (PSI) is greater than 250, 350, 450, or 550.

In some embodiments, the Polyfunctional Strength Index (PSI) is obtained by a method comprising (i) determining a desired percentage of Polyfunctional T cells; and (ii) obtaining a pre-determined cytokine profile.

In some embodiments, the effective dose comprises a dose of PSI obtained by multiplying the polyfunctional strength index by the total number of T cells. In some embodiments, the effective dose comprises at least $3.5 \times 10^{10}$ or at least $7.7 \times 10^{10}$ in units of PSI×T cells infused.

In some embodiments, the predetermined amount of polyfunctional T cells comprises at least $2.4 \times 10^7$ or at least $4.2 \times 10^7$ polyfunctional T cells.

In some embodiments, the effective dose is adjusted proportionally with tumor burden.

In some embodiments, the predetermined amount of polyfunctional T cells is determined using a composite index. In some embodiments, the composite index comprises at least two metrics. In some embodiments, the metrics are standardized by dividing each metric by their respective standard deviation.

In some embodiments, the composite index comprises Polyfunctional Strength Index (PSI) and/or patient serum levels of IL-15 prior to T cell infusion. In some embodiments, the composite index is obtained by a method comprising determining the Polyfunctional Strength Index (PSI) and measuring patient serum levels of IL-15 prior to T cell infusion. In some embodiments, the composite index is greater than 3.

In some embodiments, obtaining the pre-determined cytokine profile comprises measuring at least one of Granzyme B, IFN-gamma, MIP1a, Perforin, TNFa, TNFb, GMCSF, IL-2, IL-5, IL-7, IL-8, IL-9, IL-12, IL-15, IL-21, CCI-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4.

In some embodiments, obtaining the pre-determined cytokine profile comprises selecting at least one of Granzyme B, IFN-gamma, MIP1a, Perforin, TNFa, TNFb, GMCSF, IL-2, IL-5, IL-7, IL-8, IL-9, IL-12, IL-15, IL-21, CCI-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4.

In some embodiments, the chimeric receptor targets a tumor antigen.

In some embodiments, the chimeric receptor targets a tumor antigen selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C(TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers.

In some embodiments, the chimeric receptor specifically targets CD19.

In some embodiments, the chimeric receptor is a chimeric antigen receptor (CAR).

In some embodiments, the chimeric receptor is a T cell receptor (TCR).

In some embodiments, the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

In some embodiments, the malignancy is diffuse large B-cell lymphoma (DLBCL), primary mediastinal large B-cell lymphoma, high grade B-cell lymphoma, non-Hodgkin lymphoma, metastatic melanoma, transformed follicular lymphoma, follicular lymphoma, mantle cell lymphoma, and multiple myeloma.

In some embodiments, the malignancy is non-Hodgkin lymphoma.

In some embodiments, the polyfunctional CAR T cells co-secrete at least two proteins or cytokines at one time.

In some embodiments, the proteins or cytokines comprises one or more of Granzyme B, IFN-gamma, MIP1a, Perforin, TNFa, TNFb, GMCSF, IL-2, IL-5, IL-7, IL-8, IL-9, IL-12, IL-15, IL-21, CCI-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4.

In some embodiments, the malignancy is selected from at least one of diffuse large B-cell lymphoma (DLBCL), primary mediastinal large B-cell lymphoma, high grade B-cell lymphoma, non-Hodgkin lymphoma, metastatic melanoma, transformed follicular lymphoma, follicular lymphoma, mantle cell lymphoma, and multiple myeloma.

In some embodiments, the method further comprises modulating the total dose to adjust the total number of polyfunctional cells. In some embodiments, the method further comprises modulating the total dose to adjust the total Polyfunctional Strength Index (PSI).

In one aspect, the present disclosure provides a method of treating a malignancy in a patient comprising: (a) obtaining a plurality of T cells comprising one or more chimeric receptors; (b) measuring the Polyfunctional Strength Index (PSI) of the T cells; (c) preparing an effective dose comprising a predetermined amount of polyfunctional T cells; and (d) administering to the patient the effective dose comprising a predetermined amount of polyfunctional T cells.

In some embodiments, the predetermined amount of polyfunctional T cells is optimized to increase likelihood of patient responding to treatment.

In one aspect, the present disclosure provides a method of determining whether a patient will respond to chimeric receptor treatment comprising: (a) obtaining a plurality of T cells comprising a chimeric receptor; (b) determining the amount of polyfunctional T cells in the plurality of T cells; and (c) determining if the patient will respond to chimeric receptor treatment based on the amount of polyfunctional T cells.

In one aspect, the present disclosure provides a method of treating a malignancy in a patient comprising: (a) obtaining a plurality of T cells comprising one or more chimeric receptors; (b) preparing an effective dose comprising a predetermined amount of polyfunctional T cells; and (c) administering to the patient the effective dose comprising a pre-determined amount of polyfunctional T cells.

In some embodiments, the predetermined amount of polyfunctional T cells is greater than 15%, greater than 20%, greater than 20%, greater than 25%, greater than 30% polyfunctional T cell. In the predetermined amount of polyfunctional T cells is determined using the Polyfunctional Strength Index (PSI).

In some embodiments, the Polyfunctional Strength Index (PSI) is calculated by multiplying the percentage of polyfunctional cells by the sum of the mean fluorescence intensity of the proteins secreted by the polyfunctional cells. In some embodiments, the Polyfunctional Strength Index (PSI) is greater than 250, 350, 450, or 550.

In some embodiments, the Polyfunctional Strength Index (PSI) is obtained by a method comprising (i) determining a desired percentage of Polyfunctional T cells; and (ii) obtaining a pre-determined cytokine profile.

In some embodiments, the effective dose comprises a dose of PSI obtained by multiplying the Polyfunctional Strength Index by the total number of T cells. In some embodiments, the effective dose comprises at least $3.5 \times 10^{10}$ or at least $7.7 \times 10^{10}$ in units of PSI×T cells infused.

In some embodiments, the predetermined amount of polyfunctional T cells is at least $2.4 \times 10^7$ or at least $4.2 \times 10^7$ polyfunctional T cells.

In some embodiments, the effective dose is adjusted proportionally with tumor burden.

In some embodiments, the predetermined amount of polyfunctional T cells is determined using a composite index. In some embodiments, the composite index comprises at least two metrics. In some embodiments, the metrics are standardized by dividing each metric by their respective standard deviation.

In some embodiments, the composite index comprises Polyfunctional Strength Index (PSI) and/or patient serum levels of IL-15 prior to T cell infusion. In some embodiments, the composite index is obtained by a method comprising determining the Polyfunctional Strength Index (PSI) and measuring patient serum levels of IL-15 prior to T cell infusion.

In some embodiments, the composite index is greater than 3. In some embodiments, obtaining the pre-determined cytokine profile comprises measuring at least one of Granzyme B, IFN-gamma, MIP1a, Perforin, TNFa, TNFb, GMCSF, IL-2, IL-5, IL-7, IL-8, IL-9, IL-12, IL-15, IL-21, CCI-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4.

In some embodiments, obtaining the pre-determined cytokine profile comprises selecting at least one of Granzyme B, IFN-gamma, MIP1a, Perforin, TNFa, TNFb, GMCSF, IL-2, IL-5, IL-7, IL-8, IL-9, IL-12, IL-15, IL-21, CCI-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4.

In some embodiments, the chimeric receptor targets a tumor antigen. In some embodiments, the chimeric receptor targets a tumor antigen selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostate specific antigen (PSA), prostate-carcinoma tumor antigen-1

(PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C(TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers.

In some embodiments, the chimeric receptor specifically targets CD19. In some embodiments, the chimeric receptor is a chimeric antigen receptor (CAR). In some embodiments, the chimeric receptor is a T cell receptor (TCR).

In some embodiments, the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

In some embodiments, the malignancy is diffuse large B-cell lymphoma (DLBCL), primary mediastinal large B-cell lymphoma, high grade B-cell lymphoma, non-Hodgkin lymphoma, metastatic melanoma, transformed follicular lymphoma, follicular lymphoma, mantle cell lymphoma, and multiple myeloma.

In some embodiments, the malignancy is non-Hodgkin lymphoma.

In some embodiments, the polyfunctional CAR T cells co-secrete at least two proteins or cytokines at one time.

In some embodiments, the proteins or cytokines comprises one or more of Granzyme B, IFN-gamma, MIP1a, Perforin, TNFa, TNFb, GMCSF, IL-2, IL-5, IL-7, IL-8, IL-9, IL-12, IL-15, IL-21, CCl-11, IP-10, MIP1b, RANTES, IL-4, IL-10, IL-13, IL-22, TGF-b1, SCD137, SCD40L, IL-1b, IL-6, IL-17a, IL-17f, MCP-1, and MCP-4.

In some embodiments, the malignancy is selected from at least one of diffuse large B-cell lymphoma (DLBCL), primary mediastinal large B-cell lymphoma, high grade B-cell lymphoma, non-Hodgkin lymphoma, metastatic melanoma, transformed follicular lymphoma, follicular lymphoma, mantle cell lymphoma, and multiple myeloma.

In some embodiments, the method further comprises modulating the total dose to adjust the total number of polyfunctional cells.

In some embodiments, the method further comprises modulating the total dose to adjust the total Polyfunctional Strength Index (PSI).

In one aspect, the present disclosure provides a method of increasing potency of a chimeric receptor treatment comprising modulating the percentage of polyfunctional CAR T cells.

In some embodiments, the method further comprises a step of selecting and isolating the polyfunctional T cells.

In one aspect, the present disclosure provides a pharmaceutical composition comprising a plurality of T cells comprising one or more chimeric receptors, wherein the composition comprises a predetermined amount of polyfunctional T cells. In some embodiments, the composition comprises greater than 15% polyfunctional T cells. In some embodiments, the composition comprises greater than 20% polyfunctional T cells. In some embodiments, the composition comprises greater than 25% polyfunctional T cells.

In one aspect, the present disclosure provides a method of treating a malignancy in a patient comprising: (a) administering an effective dose of a chimeric receptor T cell immunotherapy to the patient, wherein the effective dose comprises a predetermined amount of polyfunctional T cells; and (b) monitoring the patient following infusion for signs and symptoms of an adverse reaction.

In one aspect, the present disclosure provides a method of reducing undesired side effects in a chimeric receptor treatment comprising modulating the percentage of polyfunctional chimeric receptor T cells as described herein.

In some embodiments, the predetermined amount of polyfunctional T cells is optimized to reduce severe adverse events. In some embodiments, the severe adverse events is grade 3+ or higher cytokine release syndrome (CRS) or grade 3+ or higher neurologic toxicity (NT). In some embodiments, the predetermined amount of polyfunctional T cells is determined using a composite index.

In some embodiments, the composite index is obtained by a method comprising determining the Polyfunctional Strength Index (PSI) and measuring patient serum levels of IL-15 prior to T cell infusion. In some embodiments, the composite index comprises index is obtained by a method comprising determining the Polyfunctional Strength Index (PSI) and measuring T cell expansion. In some embodiments, the method comprises using Polyfunctional Strength Index (PSI) to determine the likelihood a patient will develop grade 3+ toxicities.

In some embodiments, the method comprises monitoring the patient for signs and symptoms of undesired side effects of the treatment. In some embodiments, the undesired side effect is selected from the group consisting of cytokine release syndrome (CRS), a neurologic toxicity, a hypersensitivity reaction, a serious infection, a cytopenia, and hypogammaglobulinemia. In some embodiments, the signs and symptoms of the undesired side effect are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

BRIEF DESCRIPTION OF THE DRAWINGS

The drawings are for illustration purposes only, not for limitation.

FIGS. 1A and 1B show schematic representations of CAR (chimeric antigen receptor) construct configuration and treatment protocol. FIGS. 1C and 1D show product T cell polyfunctionality assessed by using ELISA (enzyme-linked immunosorbent assay) detection of proteins from each single-cell chamber after T cell stimulation. FIGS. 1E and 1F show polyfunctionality measured through a polyfunctionality strength index (PSI), spanning a pre-specified panel of 32 key immunologically relevant molecules across major categories: homeostatic/proliferative, inflammatory, chemotactic, regulatory, and immune effector. FIG. 1F shows single-cell, CAR-T polyfunctionality (left panel), secretion intensities of each CAR-T cell, and single-cell (center panel), CAR-T polyfunctional strength index (right panel).

FIGS. 3A-3F show association of CAR product polyfunctionality with CD19 recognition and clinical outcome. FIG. 3A shows PSI of CAR T cells single-cell (left panel) and CD4+(center panel) or CD8+(right-panel) subsets, ex vivo stimulated with CD19+ as compared to CD19− cells (NGFR transfected). FIGS. 3B-3E show association between objective response and product PSI, IFNγ measured in product co-culture with CD19+ cells, or major product T cell subsets defined by flow cytometry. T naïve, central memory (cm), effector memory (em) and effector cells (eff) were defined by staining for CD45RA and CCR7. FIG. 3F shows individual p values (Mann Whitney U test) from FIGS. 3B-3E corresponding to the strength of association of major product attributes with clinical response.

FIGS. 4A (CD4+) and 4B (CD8+) show single-cell proteomics analysis of a panel of 32 secreted cytokines, chemokines, and cytotoxic molecules was performed on product T cells from 20 patients treated with CAR T cells. The analysis was performed on all product cells, or select CD4+ and CD8+ T cells. The product T cells were first stimulated with CD19-expressing target cells or control NGFR cells before the analysis. The graphs show PSI (mean±SE) with or without CD19 stimulation for all cells, and for CD4+ and CD8+ subsets separately. The main cytokine drivers for each product T cell subpopulation are also shown. FIGS. 4C (IL-8, IL-5, IL-17a, IFN-γ, MIP-1α) and 4D (MIP-1a, IFN-γ, IL-8, Granzyme B) show product CD4+(FIG. 4C) and CD8+(FIG. 4D) T cell PSI profiles by cytokine, between patient groups with no response and OR to CAR T cell therapy. CD4 and CD8 cytokines that were up-regulated relative to mock stimulation are shown. Each cytokine PSI level reflects its average secretion intensity in polyfunctional single cells. The diagram shows the cytokines that contribute to the polyfunctionality index in the CD8+ and CD4+ T cell populations.

FIGS. 5A-5E show PSI in conjunction with CAR T cell expansion in vivo or in conjunction with conditioning-driven IL-15 pre-CAR T cell infusion correlates with objective response (OR). CAR T cell levels in blood measured by qPCR were correlated with clinical outcome. Whole pre-infusion product PSI alone (FIG. 5A), peak post-infusion CAR levels in blood alone (FIG. 5B), or product PSI combined with peak CAR levels (FIG. 5C), are shown in association with OR. Pre-CAR T cell infusion (day 0) IL-15 serum levels alone (FIG. 5D) or combined with product PSI (FIG. 5E) are shown in association with OR. Statistical values were computed using the Mann Whitney U test (P values were not adjusted for multiplicity).

FIG. 7A) or show association between day 0 IL-15 levels in serum and OR (FIG. 7B). CAR T cell levels in blood were measured by qPCR. A composite index integrating PSI and CAR T cell expansion in vivo was associated with response outcome (R=response; N=no response). Whole-product PSI, CD4+ PSI, and IL-17A PSI indexes were all evaluated in conjunction with CAR peak levels. Joint PSI and day 0 IL-15 level metrics were calculated similarly. Statistical values were computed using the Mann Whitney U test (P values were not adjusted for multiplicity).

FIGS. 11A-11F show association between PSI in conjunction with pre-treatment IL-15 levels in blood, and grade 3+NE. IL-15 levels in blood were measured by ELISA and correlated with grade 3+ AEs. A composite index integrating PSI and IL-15 levels was developed and associated with grade 3+NE or CRS, respectively. Whole-product PSI, CD4+ PSI, and IL-17A PSI were all evaluated in conjunction with IL-15 levels. Statistical values were computed using the Mann Whitney U test. P values were not adjusted for multiplicity.

FIGS. 12A-12F show Association between PSI in conjunction with pre-treatment IL-15 levels in blood, and grade 3+ CRS. IL-15 levels in blood were measured by ELISA and correlated with grade 3+ AEs. A composite index integrating PSI and IL-15 levels was developed and associated with grade 3+NE or CRS, respectively. Whole-product PSI, CD4+ PSI, and IL-17A PSI were all evaluated in conjunction with IL-15 levels. Statistical values were computed using the Mann Whitney U test. P values were not adjusted for multiplicity.

Figure 13:
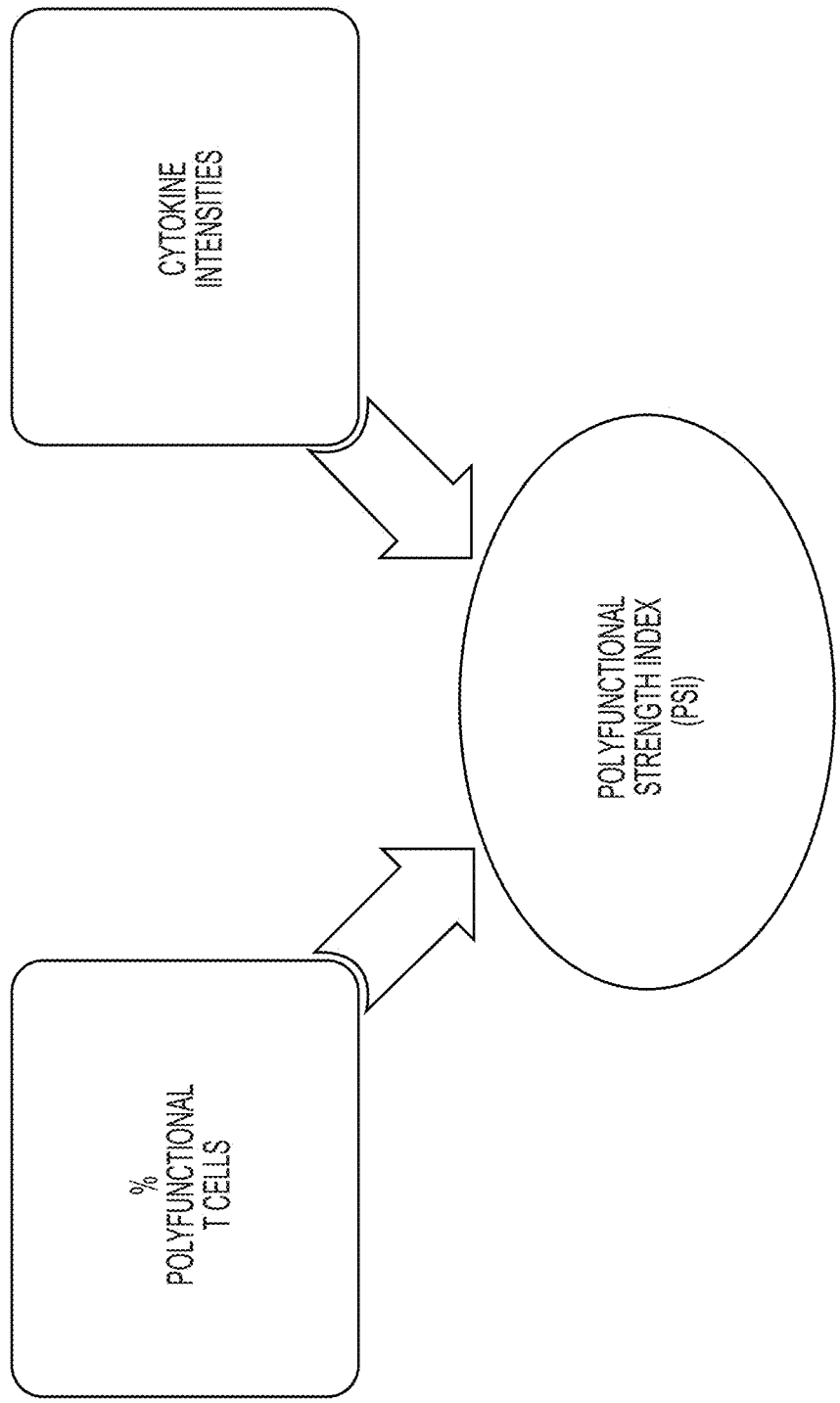

FIG. 13 shows a general schematic overview of the factors considered when calculating the PSI.

Figure 14:
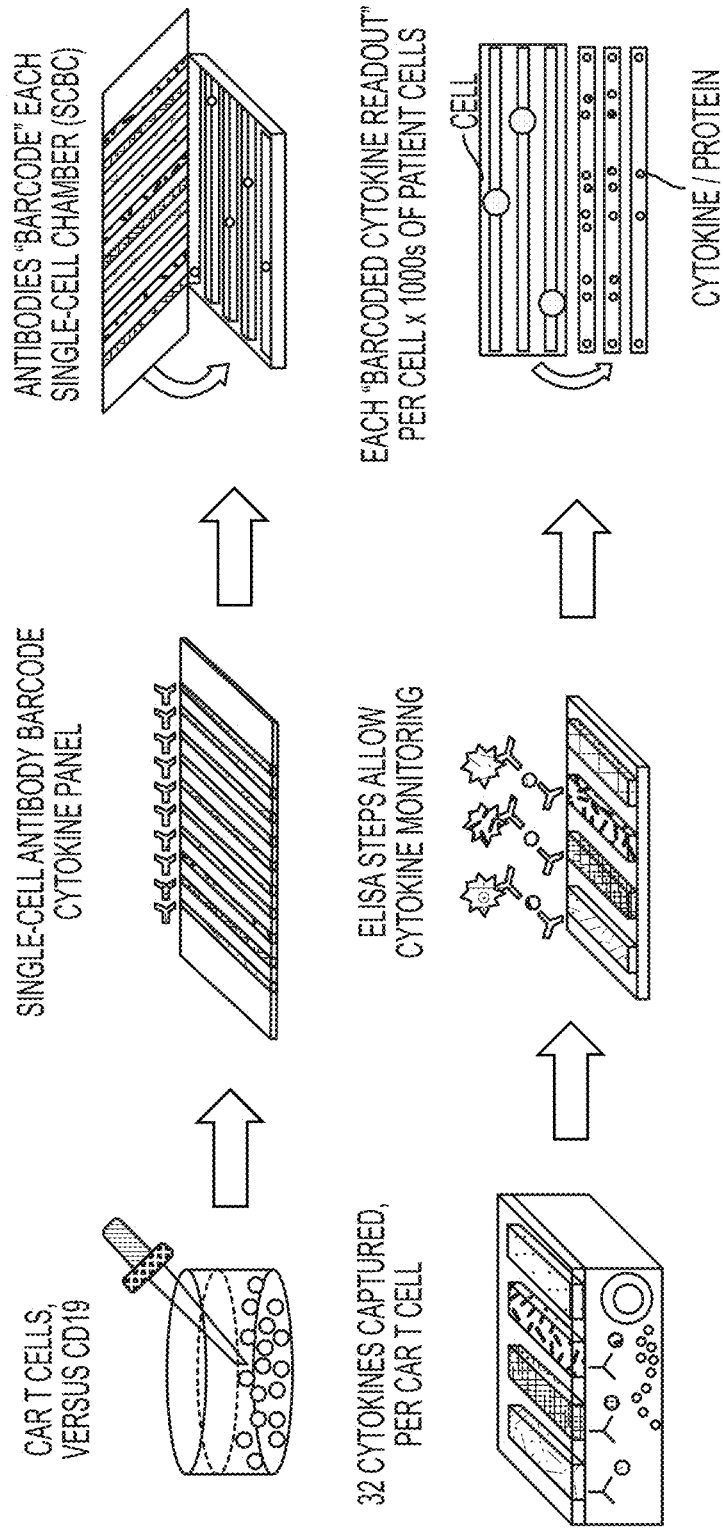

FIG. 14 shows a schematic of the analysis of pre-fusion CAR T cells polyfunctionality using the IsoPlexis Single-Cell, High Multiplexing ELISA System.

DETAILED DESCRIPTION

The present disclosure relates to methods of treating a malignancy in a patient by administering an effective dose of polyfunctional engineered T cells comprising chimeric receptors. As described herein, the polyfunctionality of engineered T cells can be used to determine the likelihood of clinical response and toxicity. In some aspects, the polyfunctionality of the engineered cells can be used to modulate or optimize the effective dose to treat the malignancy in the patient. As described herein, the polyfunctional profile of pre-infusion chimeric receptor product T cell can be used to determine the effective dose to influence clinical outcomes of chimeric receptor (e.g., CAR or TCR) T cell therapy.

After treatment with chimeric antigen receptor (CAR) T cell therapy, Interleukin (IL)-15 elevation and CAR T cell expansion have associated with non-Hodgkin lymphoma (NHL) outcomes. As described herein, single-cell analysis of the pre-infusion CAR product from patients with NHL demonstrated that CAR products contain polyfunctional T cell subsets, capable of deploying multiple immune programs represented by cytokines and chemokines such as IFNγ, IL-17A, IL-8 and MIP1a. A pre-specified T cell polyfunctionality strength index (PSI), applied to pre-infusion CAR product associated significantly with clinical response, and PSI combined with CAR T cell expansion or pre-treatment serum IL-15 levels conferred additional significance. Within the total product cell population, associations with clinical outcomes were greater with polyfunctional CD4+ T cells compared with CD8+ cells. Grade 3+ cytokine release syndrome was influenced by polyfunctional T cells, and both grade 3+ neurologic toxicity and anti-tumor efficacy were influenced by polyfunctional IL-17A-producing T cells.

Genetic reprograming of T cells to express a chimeric receptor (e.g., CAR or TCR) offers a novel approach for treating hematologic malignancies. T cells transduced with an anti-CD19 CAR composed of CD28 and CD3ζ signaling domains produce interferon (IFN)-γ in a CD19-specific manner, kill primary leukemia cells, and undergo CD19-target dependent proliferation. Treatment of B cell malignancies with anti-CD19 CAR T cells results in durable remissions in a significant number of patients. This treatment is associated with B cell aplasia due to endogenous CD19 expression on B cells. Additionally, treatment with anti-CD19 CAR T cell therapy can cause cytokine release syndrome (CRS) and neurological events (NE).

The methods described herein are based on the surprising discovery that CAR T cells orchestrate clinical activity by deploying multiple immune programs that complement each other from a functional perspective. The functionality of CAR T cell products is determined by using a high-content single-cell multiplex cytokine analysis. The polyfunctional evaluation allowed identified a subset of polyfunctional T cells in CAR T cell products—those that are capable of producing 2 or more cytokines upon stimulation with antigen in vitro. In addition, associations of a pre-specified polyfunctionality strength index (PSI) applied to CAR T cell products, with CAR T cell expansion in vivo, objective response, and toxicities. Highly polyfunctional T cells within CAR T cell products are significantly associated with clinical response and that a subset of polyfunctional CD4+ T cells that produce IL-17A is associated with grade 3 or higher NE.

Definitions

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. "About" or "approximately" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In some embodiments, antigens are tumor antigens.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods disclosed herein include, but are not limited to, cancers of the immune system including lymphoma, leukemia, myeloma, and other leukocyte malignancies. In some embodiments, the methods disclosed herein can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. The particular cancer can be responsive to chemo- or radiation therapy or the cancer can be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, "chimeric receptor" refers to an engineered surface expressed molecule capable of recognizing a particular molecule. Chimeric antigen receptors (CARs) and engineered T cell receptors (TCRs), which comprise binding domains capable of interacting with a particular tumor antigen, allow T cells to target and kill cancer cells that express the particular tumor antigen.

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naïve cells, are CD45RO−, CCR7+, CD45RA+, CD62L+(L-selectin), CD27+, CD28+ and IL-7Ra+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv can be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CAR T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell can include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD1 1a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission.

As used herein, "Polyfunctional T cells" refers to cells co-secreting at least two proteins from a pre-specified panel per cell coupled with the amount of each protein produced (i.e., combination of number of proteins secreted and at what intensity). In some embodiments, a single cell functional profile is determined for each evaluable product. Profiles can be categorized into effector (Granzyme B, IFN-γ, MIP-1α, Perforin, TNF-α, TNF-β), stimulatory (GM-CSF, IL-2, IL-5, IL-7, IL-8, IL-9, IL-12, IL-15, IL-21), regulatory (IL-4, IL-10, IL-13, IL-22, TGF-β1, sCD137, sCD40L), chemoattractive (CCL-11, IP-10, MIP-1β, RANTES), and inflammatory (IL-1b, IL-6, IL-17A, IL-17F, MCP-1, MCP-4) groups. In some embodiments, the functional profile of each cell enables the calculation of other metrics, including a breakdown of each sample according to cell polyfunctionality (i.e., what percentage of cells are secreting multiple cytokines versus non-secreting or monofunctional cells), and a breakdown of the sample by functional groups (i.e., which mono- and polyfunctional groups are being secreted by cells in the sample, and their frequency).

Various aspects of the disclosure are described in further detail in the following subsections.

Polyfunctionality and the Polyfunctional Strength Index (PSI)

The polyfunctionality strength index (PSI) measures polyfunctionality by incorporating cytokine intensities and percentage of polyfunctional cells (FIG. 13). In some embodiments, the polyfunctional strength index (PSI) measures polyfunctionality, spanning a pre-specified panel of 32 key immunologically relevant molecules across major categories: homeostatic/proliferative, inflammatory, chemotactic, regulatory, and immune effector. In some embodiments, cytokine intensities can be measured by ELISA (FIG. 14)

As shown below, PSI can be defined as the percentage of polyfunctional cells, multiplied by mean fluorescence intensity (MFI) of the proteins secreted by those cells:

$$PSI_{sample} = (\% \text{ polyfunctional cells in sample})$$
$$\sum_{i=1}^{32} MFI \text{ of secreted protein } i \text{ of the polyfunctional cells}$$

Whole-product PSI, CD4+ PSI, and IL-17A PSI indexes can also be evaluated in conjunction with CAR peak levels. A composite index integrating PSI and CAR T cell expansion in vivo was developed and was associated with objective response (OR). To generate the composite index, the metrics were added to each other after each was first standardized to have unit variance. This standardization was achieved by dividing the metrics by their respective standard deviation to bring them to a common magnitude/scale.

In some embodiments, objective response (OR) is determined per the revised IWG Response Criteria for Malignant Lymphoma (Cheson, 2007) and determined by IWG Response Criteria for Malignant Lymphoma (Cheson et al. *Journal of Clinical Oncology* 32, no. 27 (September 2014) 3059-3067). Duration of Response is assessed. The Progression-Free Survival (PFS) by investigator assessment per Lugano Response Classification Criteria is evaluated.

In some embodiments, the amount of polyfunctional cells (e.g., determined by PSI, percentage of polyfunctional cells in sample, combined indices) is used to determine an effective dose.

In some embodiments, the percentage of polyfunctional cells in the sample is greater than approximately 10%, 15%, 20%, 25%, 30%, 35%, 40%, or 50%.

In some embodiments, the percentage of polyfunctional cells in the sample is less than approximately 70%, 60%, 50%, 40%, 30%, 29%, 28%, 27%, 26%, 25%, 24%, 23%, 22%, 21%, 20% or 15%. In some embodiments, the percentage of polyfunctional cells in the sample ranges between approximately 10-50%, 15-45%, 20-40%, 25-35%, 15-30%, 15-25%, 20-30%, or 20-25%.

In some embodiments, the PSI is greater than 250, greater than 260, greater than 270, greater than 280, greater than 290, greater than 300, greater than 310, greater than 320, greater than 330, greater than 340, greater than 350, greater than 360, greater than 370, greater than 380, greater than 390, greater than 400, greater than 410, greater than 420, greater than 430, greater than 440, greater than 450, greater than 460, greater than 470, greater than 480, greater than 490, greater than 500, greater than 510, greater than 520, greater than 530, greater than 540, greater than 550, greater than 560, greater than 570, greater than 580, greater than 590, or greater than 600.

In some embodiments, the maximum PSI is 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600.

In some embodiments, the PSI ranges from approximately 250-600, 250-590, 250-580, 250-570, 250-260, 250-550, 250-540, 250-530, 250-520, 250-510, 250-500, 250-490, 250-480, 250-470, 250-460, 250-450, 250-440, 250-430, 250-420, 250-410, 250-400, 250-390, 250-380, 250-370, 250-360, 250-350, 250-340, 250-330, 250-320, 250-310, 250-300, 300-600, 300-590, 300-580, 300-570, 300-560, 300-550, 300-540, 300-530, 300-520, 300-510, 300-500, 300-490, 300-480, 300-470, 300-460, 300-450, 300-400, 350-450, 450-600, or 550-600.

In some embodiments, the predetermined amount of polyfunctional T cells is determined using a composite index comprising at least two metrics (e.g., Polyfunctional Strength Index (PSI) and patient serum levels of IL-15 prior to T cell infusion). In some embodiments, the composite index is greater than 3, greater than 4, greater than 5, or greater than 6. In some embodiments, the composite index is at least 2. In some embodiments, the composite index ranges from approximately 2-6, 3-6, 4-6, or 5-6.

Chimeric Antigen Receptors and T Cell Receptors

Chimeric antigen receptors (CARs or CAR-Ts) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell. Chimeric antigen receptors incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci. Transl. Med. 3:95 (2011); Porter et al., N. Engl. J. Med. 365:725-33 (2011), and Gross et al., Annu. Rev. Pharmacol. Toxicol. 56:59-83 (2016).

In some embodiments, a costimulatory domain which includes a truncated hinge domain ("THD") further comprises some or all of a member of the immunoglobulin family such as IgG1, IgG2, IgG3, IgG4, IgA, IgD, IgE, IgM, or fragment thereof.

In some embodiments, the THD is derived from a human complete hinge domain ("CHD"). In other embodiments, the THD is derived from a rodent, murine, or primate (e.g., non-human primate) CHD of a costimulatory protein. In some embodiments, the THD is derived from a chimeric CHD of a costimulatory protein.

The costimulatory domain for the CAR or TCR of the invention can further comprise a transmembrane domain and/or an intracellular signaling domain. The transmembrane domain can be designed to be fused to the extracellular domain of the CAR. It can similarly be fused to the intracellular domain of the CAR. In some embodiments, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain can be derived either from a natural or from a synthetic source. Where the source is natural, the domain can be derived from any membrane-bound or transmembrane protein. Transmembrane regions of particular use in this invention can be derived from (i.e., comprise) 4-1BB/ CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD1 1a, CD1 1b, CD1 1c, CD1 1d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/ RANKL, VLA1, or VLA-6, or a fragment, truncation, or a combination thereof.

Optionally, short linkers can form linkages between any or some of the extracellular, transmembrane, and intracellular domains of the CAR. In some embodiments, the linker may be derived from repeats of glycine-glycine-glycine-glycine-serine (G4S)n or GSTSGSGKPGSGEGSTKG (SEQ ID NO: 1). In some embodiments, the linker comprises 3-20 amino acids and an amino acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to GSTSGSGKPGSGEGSTKG (SEQ ID NO: 1).

The linkers described herein, may also be used as a peptide tag. The linker peptide sequence can be of any appropriate length to connect one or more proteins of interest and is preferably designed to be sufficiently flexible so as to allow the proper folding and/or function and/or activity of one or both of the peptides it connects. Thus, the linker peptide can have a length of no more than 10, no more than 11, no more than 12, no more than 13, no more than 14, no more than 15, no more than 16, no more than 17, no more than 18, no more than 19, or no more than 20 amino acids. In some embodiments, the linker peptide can have a length of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the linker comprises at least 7 and no more than 20 amino acids, at least 7 and no more than 19 amino acids, at least 7 and no more than 18 amino acids, at least 7 and no more than 17 amino acids, at least 7 and no more than 16 amino acids, at least 7 and no more 15 amino acids, at least 7 and no more than 14 amino acids, at least 7 and no more than 13 amino acids, at least 7 and no more than 12 amino acids or at least 7 and no more than 11 amino acids. In certain embodiments, the linker comprises 15-17 amino acids, and in particular embodiments, comprises 16 amino acids. In some embodiments, the linker comprises 10-20 amino acids. In some embodiments, the linker comprises 14-19 amino acids. In some embodiments, the linker comprises 15-17 amino acids. In some embodiments, the linker comprises 15-16 amino acids. In some embodiments, the linker comprises 16 amino acids. In some embodiments, the linker comprises 3, 4, 5, 6, 7, 8, 9, 10, 11, 12, 13, 14, 15, 16, 17, 18, 19 or 20 amino acids.

In some embodiments, a spacer domain is used. In some embodiments, the spacer domain is derived from CD4, CD8a, CD8b, CD28, CD28T, 4-1BB, or other molecule described herein. In some embodiments, the spacer domains may include a chemically induced dimerizer to control expression upon addition of a small molecule. In some embodiments, a spacer is not used.

The intracellular (signaling) domain of the engineered T cells of the invention can provide signaling to an activating domain, which then activates at least one of the normal effector functions of the immune cell. Effector function of a T cell, for example, can be cytolytic activity or helper activity including the secretion of cytokines.

In certain embodiments, suitable intracellular signaling domain include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8, CD8alpha, CD8beta, CD96 (Tactile), CD1 1a, CD1 1b, CD1 1c, CD1 1d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that specifically binds with CD83, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

A TCR may be introduced to convey antigen reactivity. In some embodiments, the antigen reactivity is restricted by MHC presentation of a peptide. The TCR may be an alpha/beta TCR, gamma/delta TCR, or other. In some embodiments, the TCR is an HPV-16 E7 TCR with murine constant chains (2A linked). In some embodiments, the chains may be linked by an IRES or any 2A family members' sequence (e.g., P2A, T2A, E2A, F2A, etc.). In some embodiments, the TCR is an HPV recognizing TCR, or other viral reactive TCR (e.g., EBV, influenza, etc.). In some embodiments, a cancer or cancer associated antigen reactive TCR may be used (e.g., NYESO, MART1, gp100, etc.)

In some embodiments, the TCR is a TCR of normal/ healthy peptide reactivity or other antigen reactivity/restriction. In some embodiments, the TCR is reactive against murine or other non-human MHC. In some embodiments, the TCR is a class I or class II restricted TCR.

Antigen Binding Molecules

Suitable CARs can be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). A scFv is a single chain antibody fragment having the variable regions of the heavy and light chains of an antibody linked together. See U.S. Pat. Nos. 7,741,465 and 6,319,494, as well as Eshhar et al., Cancer Immunol Immunotherapy (1997) 45: 131-136. A scFv retains the parent antibody's ability to interact specifically with target antigen. scFv's are useful in chimeric antigen receptors because they can be engineered to be expressed as part of a single chain along with the other CAR components. Id. See also Krause et al., J. Exp. Med., Volume 188, No. 4, 1998 (619-626); Finney et al., *Journal of Immunology*, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the polynucleotide encodes a CAR or a TCR comprising a THD of the present invention and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C(TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers.

Engineered T Cells and Uses

The cell of the present disclosure may be obtained through T cells obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naïve, memory, and effector T cell subpopulations either before or after genetic modification and/or expansion.

In some embodiments, CD8+ cells are further sorted into naïve, central memory, and effector cells by identifying cell surface antigens that are associated with each of these types of CD8+ cells. In some embodiments, the expression of phenotypic markers of central memory T cells includes expression of CCR7, CD3, CD28, CD45RO, CD62L, and CD127 and negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+T helper cells can be sorted into naïve, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR or TCR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and co-stimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor.

In some embodiments, the composition comprises a pharmaceutically acceptable carrier, diluent, solubilizer, emulsifier, preservative and/or adjuvant. In some embodiments, the composition comprises an excipient.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method can include collecting blood cells from the patient. The isolated blood cells (e.g., T cells) can then be engineered to express a CAR or a TCR disclosed herein. In a particular embodiment, the CAR T cells or the TCR T cells are administered to the patient. In some embodiments, the CAR T cells or the TCR T cells treat a tumor or a cancer in the patient. In some embodiments the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

In some embodiments, the T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, the therapeutically effective amount of the CAR-positive viable T cells is between about $1\times10^6$ and about $2\times10^6$ CAR-positive viable T cells per kg body weight up to a maximum dose of about $1\times10^8$ CAR-positive viable T cell.

Methods of Treatment

The methods disclosed herein can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistiocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is leukemia. In some embodiments, the cancer is acute myeloid leukemia.

In some embodiments, the methods further comprise administering a chemotherapeutic. In some embodiments, the chemotherapeutic selected is a lymphodepleting (pre-conditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m²/day and 2000 mg/m²/day) and specified doses of fludarabine (between 20 mg/m²/day and 900 mg/m²/day). One such dose regimen involves treating a patient comprising administering daily to the patient about 500 mg/m²/day of cyclophosphamide and about 60 mg/m²/day of fludarabine for three days prior to administration of a therapeutically effective amount of engineered T cells to the patient.

In some embodiments, the antigen binding molecule, transduced (or otherwise engineered) cells (such as CARs or TCRs), and the chemotherapeutic agent are administered each in an amount effective to treat the disease or condition in the subject.

In some embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche).

Additional therapeutic agents suitable for use in combination with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR immune cells are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAID s include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Administration

In some embodiments, engineered T cells described herein are used to treat a malignancy in a patient comprising: (a) obtaining a plurality of T cells comprising one or more chimeric receptors; and (b) administering an effective dose of the T cells to the patient, wherein the effective dose comprises a predetermined amount of polyfunctional T cells.

In some embodiments, the T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg.

In some embodiments, the therapeutically effective amount of the CAR-positive viable T cells is between about $1 \times 10^6$ and about $2 \times 10^6$ CAR-positive viable T cells per kg body weight up to a maximum dose of about $1 \times 10^8$ CAR-positive viable T cell.

In some embodiments, the therapeutically effective amount or dose is determined by the amount of polyfunctional T cells. The amount of polyfunctional T cells can be at least about $10^4$ polyfunctional cells, at least about $10^5$ polyfunctional cells, at least about $10^6$ polyfunctional cells, at least about $10^7$ polyfunctional cells, at least about $10^8$ polyfunctional cells, at least about $10^9$ polyfunctional cells, or at least about $10^{10}$ polyfunctional cells.

In some embodiments, the effective dose comprises a dose of PSI obtained by multiplying the polyfunctional strength index by the total number of T cells. In some embodiments, the effective dose comprises at least $3.5 \times 10^{10}$ or at least $7.7 \times 10^{10}$. In some embodiments, the predetermined amount of polyfunctional T cells is obtained by multiplying the polyfunctional strength index by the total number of cells (e.g., about $2 \times 10^6$ viable T cells per kg body weight up to a maximum dose of about $1 \times 10^8$ viable T cell). In some embodiments, the effective dose ranges from approximately $3.5 \times 10^{10}$ to $7.7 \times 10^{10}$ polyfunctional T cells. In some embodiments, the effective dose of PSI ranges from at approximately $3.5 \times 10^{10}$ to $4.5 \times 10^{10}$, $3.5 \times 10^{10}$ to $5.5 \times 10^{10}$, $3.5 \times 10^{10}$ to $6.5 \times 10^{10}$, $3.5 \times 10^{10}$ to $7.5 \times 10^{10}$, $3.5 \times 10^{10}$ to $7.8 \times 10^{10}$, $3.5 \times 10^{10}$ to $8.0 \times 10^{10}$, $3.5 \times 10^{10}$ to $9.0 \times 10^{10}$, $3.5 \times 10^{10}$ to $10.0 \times 10^{10}$, $4.5 \times 10^{10}$ to $5.5 \times 10^{10}$, $4.5 \times 10^{10}$ to $6.5 \times 10^{10}$, $4.5 \times 10^{10}$ to $7.5 \times 10^{10}$, $4.5 \times 10^{10}$ to $7.8 \times 10^{10}$, $4.5 \times 10^{10}$ to $8.0 \times 10^{10}$, $4.5 \times 10^{10}$ to $9.0 \times 10^{10}$, $4.5 \times 10^{10}$ to $10.0 \times 10^{10}$, $5.5 \times 10^{10}$ to $6.5 \times 10^{10}$, $5.5 \times 10^{10}$ to $7.5 \times 10^{10}$, $5.5 \times 10^{10}$ to $7.8 \times 10^{10}$, $5.5 \times 10^{10}$ to $8.0 \times 10^{10}$, $5.5 \times 10^{10}$ to $9.0 \times 10^{10}$, $5.5 \times 10^{10}$ to $10.0 \times 10^{10}$, $6.5 \times 10^{10}$ to $7.5 \times 10^{10}$, $6.5 \times 10^{10}$ to $7.8 \times 10^{10}$, $6.5 \times 10^{10}$ to $8.0 \times 10^{10}$, $6.5 \times 10^{10}$ to $9.0 \times 10^{10}$, $6.5 \times 10^{10}$ to $10.0 \times 10^{10}$, $7.5 \times 10^{10}$ to $8.0 \times 10^{10}$, $7.5 \times 10^{10}$ to $9.0 \times 10^{10}$, $7.5 \times 10^{10}$ to $10.0 \times 10^{10}$ in units of PSI×T cells infused.

In some embodiments, the effective dose comprises at least approximately $3.0 \times 10^{10}$, $3.1 \times 10^{10}$, $3.2 \times 10^{10}$, $3.3 \times 10^{10}$, $3.4 \times 10^{10}$, $3.5 \times 10^{10}$, $3.6 \times 10^{10}$, $3.7 \times 10^{10}$, $3.8 \times 10^{10}$, $3.9 \times 10^{10}$, $4.0 \times 10^{10}$, $4.1 \times 10^{10}$, $4.2 \times 10^{10}$, $4.3 \times 10^{10}$, $4.4 \times 10^{10}$, $4.5 \times 10^{10}$, $4.6 \times 10^{10}$, $4.7 \times 10^{10}$, $4.8 \times 10^{10}$, $4.9 \times 10^{10}$, $5.0 \times 10^{10}$, $5.1 \times 10^{10}$, $5.2 \times 10^{10}$, $5.3 \times 10^{10}$, $5.4 \times 10^{10}$, $5.5 \times 10^{10}$, $5.6 \times 10^{10}$, $5.7 \times 10^{10}$, $5.8 \times 10^{10}$, $5.9 \times 10^{10}$, $6.0 \times 10^{10}$, $6.1 \times 10^{10}$, $6.2 \times 10^{10}$, $6.3 \times 10^{10}$, $6.4 \times 10^{10}$, $6.5 \times 10^{10}$, $6.6 \times 10^{10}$, $6.7 \times 10^{10}$, $6.8 \times 10^{10}$, $6.9 \times 10^{10}$, or $7.0 \times 10^{10}$, $7.1 \times 10^{10}$, $7.2 \times 10^{10}$, $7.3 \times 10^{10}$, $7.4 \times 10^{10}$, $7.5 \times 10^{10}$, $7.6 \times 10^{10}$, $7.7 \times 10^{10}$, $7.8 \times 10^{10}$, $7.9 \times 10^{10}$, $8.0 \times 10^{10}$ in units of PSI× T cells infused. In some embodiments, the effective dose comprises at least approximately $3.5 \times 10^{10}$ in units of PSI×T cells infused. In some embodiments, the effective dose comprises at least approximately $7.7 \times 10^{10}$ in units of PSI×T cells infused.

In some embodiments, the predetermined amount of polyfunctional T cells is obtained by multiplying the percentage of polyfunctional T cells by the total number of cells (e.g., about $2 \times 10^6$ viable T cells per kg body weight up to a maximum dose of about $1 \times 10^8$ viable T cell). In some embodiments, the predetermined amount of polyfunctional T cells is at least approximately $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $2.1 \times 10^7$, $2.2 \times 10^7$, $2.3 \times 10^7$, $2.4 \times 10^7$, $2.5 \times 10^7$, $2.6 \times 10^7$, $2.7 \times 10^7$, $2.8 \times 10^7$, $2.9 \times 10^7$, $3.0 \times 10^7$, $3.1 \times 10^7$, $3.2 \times 10^7$, $3.3 \times 10^7$, $3.4 \times 10^7$, $3.5 \times 10^7$, $3.6 \times 10^7$, $3.7 \times 10^7$, $3.8 \times 10^7$, $3.9 \times 10^7$, $4.0 \times 10^7$, $4.1 \times 10^7$, $4.2 \times 10^7$, $4.3 \times 10^7$, $4.4 \times 10^7$, $4.5 \times 10^7$, $4.6 \times 10^7$, $4.7 \times 10^7$, $4.8 \times 10^7$, $4.9 \times 10^7$, or $5.0 \times 10^7$ polyfunctional T cells. In some embodiments, the predetermined amount of polyfunctional T cells ranges from approximately $2.4 \times 10^7$ to $4.2 \times 10^7$. In some embodiments, the predetermined amount of polyfunctional T cells ranges from approximately $2.0 \times 10^7$ to $5.0 \times 10^7$, $2.0 \times 10^7$ to $4.5 \times 10^7$, $2.0 \times 10^7$ to $4.0 \times 10^7$, and $1.0 \times 10^7$ to $3.5 \times 10^7$ polyfunctional T cells.

Monitoring

In some embodiments, administration of chimeric receptor T cell immunotherapy occurs at a certified healthcare facility.

In some embodiments, the methods disclosed herein comprise monitoring patients at least daily for 7 days at the certified healthcare facility following infusion for signs and symptoms of CRS and neurologic toxicities.

In some embodiments, patients are instructed to remain within proximity of the certified healthcare facility for at least 4 weeks following infusion.

Management of Severe Adverse Reactions

In some embodiments, the method comprises management of adverse reactions. In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

Cytokine Release Syndrome

In some embodiments, the method comprises preventing or reducing the severity of CRS in a chimeric receptor treatment by modulating the percentage of polyfunctional CAR T cells. In some embodiments, the polyfunctional T cells are deactivated after administration to the patient.

In some embodiments, the method comprises identifying CRS based on clinical presentation. In some embodiments, the method comprises evaluating for and treating other causes of fever, hypoxia, and hypotension. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered.

In some embodiments, the method comprises monitoring patients at least daily for 7 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

Neurologic Toxicity

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life threatening neurologic toxicities.

In some embodiments, the method comprises monitoring patients at least daily for 7 days at the certified healthcare facility following infusion for signs and symptoms of neurologic toxicities. In some embodiments, the method comprises monitoring patients for signs or symptoms of neurologic toxicities for 4 weeks after infusion.

Secondary Malignancies

In some embodiments, patients treated with CD19-directed genetically modified autologous T cell immunotherapy may develop secondary malignancies. In some embodiments, the method comprises monitoring life-long for secondary malignancies.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The present invention is further illustrated by the following examples, which should not be construed as further limiting. The contents of all references cited throughout this application are expressly incorporated herein by reference.

EXAMPLES

Example 1: Patient Demographics and Product Characterization

Pre-Infusion CAR T Cell Product Polyfunctional Profiles are Associated with Clinical Response and Toxicities The study (NCT00924326) cohort comprised 22 patients with recently described clinical outcomes. Of the 22 treated patients, 19 had diffuse large B cell lymphoma (DLBCL), 2 had follicular lymphoma, and 1 had mantle cell lymphoma (Table 1). Of the 19 patients with DLBCL, 11 had chemotherapy refractory lymphoma. Five other patients with DLBCL had lymphoma that had relapsed 10 months or less after autologous stem cell transplant (ASCT) as their last treatment before protocol enrollment. Eleven patients with DLBCL were high risk, according to the second-line, age-adjusted International Prognostic Index. (Hamlin, P. A. et al. Age-adjusted International Prognostic Index predicts autologous stem cell transplantation outcome for patients with relapsed or primary refractory diffuse large B-cell lymphoma. *Blood* 102, 1989-1996.) The median number of unique lymphoma therapies received before protocol enrollment was 4 (range, 1 to 7). Objective response (OR) is defined as partial (PR) or complete (CR) defined by Cheson 2014 criteria (Cheson et al. *Journal of Clinical Oncology* 32, no. 27 (September 2014) 3059-3067). Stable (SD) and progressive disease (PD) correspond to lack of objective response (non-responders). Products from 20 patients in this cohort were evaluable by single-cell multiplex cytokine profiling. NE and cytokine release syndrome (CRS) were graded as previously reported. (Kochenderfer, J. N. et al. Lymphoma remissions caused by anti-CD19 chimeric antigen receptor T cells are associated with high serum interleukin-15 levels. *J Clin Oncol* 35, 1803-1813 (2017). Epub 2017 Mar. 14.). As shown in Table 1, major demographic characteristics of the evaluable patients: age, gender and tumor histology (diffuse large B cell lymphoma—DLBCL, transformed follicular lymphoma—TFL, mantle cell lymphoma—MCL, follicular lymphoma—FL); the best response by Cheson criteria (BRESP), and whether the subject had Grade 3+ neurologic toxicity (marked NT in Table 1) or Grade 3+ cytokine release syndrome (marked CRS in Table 1).

TABLE 1

Patient demographics, clinical response and adverse events.

| ID | Age | Sex | Lymphoma | Lymphoma Category | # Prior Lines of Therapy | BRESP | OR Subgroup | Grade 3+ CRS | Grade 3+ NT |
|---|---|---|---|---|---|---|---|---|---|
| 1 | 66.5 | M | DLBCL | Aggressive | 3 | PR | OR | CRS | — |
| 2 | 63.5 | M | FL | Indolent | 6 | CR | OR | CRS | NT |
| 3 | 65.3 | M | DLBCL | Aggressive | 4 | PR | OR | CRS | — |
| 4 | 47.1 | M | DLBCL | Aggressive | 2 | PR | OR | — | — |
| 5 | 28.8 | M | DLBCL | Aggressive | 7 | PD | — | — | — |
| 6 | 62.7 | M | DLBCL | Aggressive | 7 | CR | OR | — | NT |
| 7 | 54.7 | M | DLBCL | Aggressive | 3 | PD | — | CRS | — |
| 8 | 28.6 | M | DLBCL | Aggressive | 2 | SD | — | — | — |
| 9 | 29.5 | M | PMBCL | Aggressive | 3 | SD | — | — | — |
| 10 | 40.4 | M | PMBCL | Aggressive | 2 | PD | — | — | NT |
| 11 | 67.8 | M | DLBCL | Aggressive | 3 | CR | OR | — | NT |
| 12 | 50.4 | M | MCL | Indolent | 1 | CR | OR | CRS | NT |
| 13 | 53.2 | M | DLBCL | Aggressive | 4 | CR | OR | CRS | NT |
| 14 | 67.0 | F | FL | Indolent | 3 | CR | OR | CRS | NT |
| 15 | 51.9 | M | DLBCL | Aggressive | 3 | CR | OR | CRS | NT |
| 16 | 52.0 | F | DLBCL | Aggressive | 5 | CR | OR | CRS | NT |
| 17 | 39.0 | M | DLBCL | Aggressive | 4 | PR | OR | CRS | NT |
| 18 | 67.1 | F | DLBCL | Aggressive | 4 | CR | OR | CRS | NT |
| 19 | 64.4 | M | DLBCL | Aggressive | 4 | CR | OR | CRS | NT |
| 20 | 52.0 | M | DLBCL | Aggressive | 5 | PD | — | CRS | — |

Clinical responses and toxicities were associated with increased CAR T cell expansion in vivo and elevated serum levels of IL-15, IL-10, and granzyme B. In response to ex vivo co-culture with CD19+ target cells, product T cells rapidly secrete a broad array of cytokines, chemokines, and immune effector molecules. These cytokines and chemokines as well as T cell characteristics defined by commonly utilized phenotypic markers in a heterogeneous population of T cells, were not significantly associated with clinical outcomes (data not shown). To determine the parameters that associate with clinical outcome in anti-CD19 CAR T cell therapy, product T cells were characterized at the single-cell level by using the polyfunctionality strength index (PSI) based on the frequency and production levels of homeostatic/proliferative, inflammatory, chemotactic, regulatory, and immune effector molecules. To perform this analysis, a single-cell barcode chip (SCBC) platform and a pre-specified formula were utilized (FIG. 14). In brief, product PSI was defined as the percentage of polyfunctional cells multiplied by mean fluorescence intensity (MFI) of the cytokines secreted by those cells (FIGS. 1A-1F).

T Cell Polyfunctionality Evaluation by Single-Cell Cytokine Profiling and Calculation of PSI Cryopreserved CAR T cell products comprising about 40-60% CAR+ T cells, measured by surface expression of the scFv by flow cytometry, were thawed and cultured in complete Cell Therapy Systems (CTS) medium with IL-2 (10 ng/mL, Biolegend) at a density of $1 \times 10^6$/mL in a 37° C., 5% $CO_2$ incubator. After overnight recovery, viable T cells were enriched using Ficoll-Paque Plus medium (Fisher Scientific). CD4+/CD8+ T cell subsets were separated using anti-CD4 or anti-CD8 microbeads (Miltenyi Biotec, Bergisch Gladbach, Germany) and then stimulated with K562 cells transduced with either CD19 or nerve growth factor receptor (NGFR) at a ratio of 1:2 for 20 hours at 37° C., 5% CO2. The co-cultured CD4+ or CD8+ T cells were further enriched by the depletion of CD19-K562 or NGFR-K562 cells by using anti-CD19 or anti-NGFR conjugated magnetic beads. To confirm the presence of CD4+ or CD8+ CAR T cells, samples were stained with Alexa Fluor 647 conjugated anti-CD4 or anti-CD8 antibody at room temperature for 10 minutes, rinsed once with phosphate-buffered saline (PBS), and resuspended in complete CTS medium at a density of $1 \times 10^6$/mL. Approximately 30 μL of cell suspension was loaded into the single-cell barcode chip (SCBC) microchip for single-cell secretomics evaluation.

For each sample, a 32-plex assay measured secreted proteins from ~2000 T cells (FIGS. 1A-1F). Raw microscopy and microarray scans of the cell samples (loaded onto the SCBC) and protein secretion data were analyzed using proprietary image processing software to determine the locations of chambers containing single cells and subsequent extraction of their secretion readouts. Data from empty cell chambers were used to measure the background intensity levels for each analyzed protein. Single-cell readouts were then normalized using the background readouts to determine significant secretions and compare profiles across assays. Proprietary software and the R statistical package were used for statistical data analysis and visualizations.

The functional profile was determined for each evaluable product. Profiles were categorized into effector (Granzyme B, IFN-γ, MIP-1α, Perforin, TNF-α, TNF-β), stimulatory (GM-CSF, IL-2, IL-5, IL-7, IL-8, IL-9, IL-12, IL-15, IL-21), regulatory (IL-4, IL-10, IL-13, IL-22, TGF-β1, sCD137, sCD40L), chemoattractive (CCL-11, IP-10, MIP-1β, RANTES), and inflammatory (IL-1b, IL-6, IL-17A, IL-17F, MCP-1, MCP-4) groups. Polyfunctional CAR product T cells were defined as cells co-secreting at least 2 proteins from the pre-specified panel per cell coupled with the amount of each protein produced (i.e., combination of number of proteins secreted and at what intensity). Cutoffs for any given cytokine were computed based on background levels in wells with zero cells+3SD. Knowing the functional profile of each cell enables the calculation of various other metrics, such as a breakdown of each sample according to cell polyfunctionality (i.e., what percentage of cells are secreting multiple cytokines, as opposed to nonsecreting or monofunctional cells), and a breakdown of the sample by functional groups (i.e., which mono- and polyfunctional groups are being secreted by cells in the sample, and their frequency).

The PSI of each sample was computed. (Ma, C. et al. Multifunctional T-cell analyses to study response and progression in adoptive cell transfer immunotherapy. Cancer Discov 3, 418-29 (2013).

The CD4+ and CD8+ PSIs were computed for the corresponding CD19-K562 or NGFR-K562 stimulated samples of each donor. An overall PSI, which is the average of the CD4+ and CD8+ PSI, was also computed.

The CD4+ PSI calculation was performed by analyzing all polyfunctional CD4+ cell readouts of the sample. Each readout was an n-dimensional vector (n=number of analyzed cytokines) of signal intensities (MFI, random fluorescence intensity). The average signal intensity of each cytokine was found across the set of polyfunctional cells. Multiplying this number by the fraction of polyfunctional cells provided the individual cytokine PSI values (e.g., IL-17A CD4+ PSI). The sum of all the individual cytokine PSI values provided the overall CD4+ PSI for the sample. The same calculation was performed to find the CD8+ PSI and each cytokine's individual CD8+ PSI. Averaging CD4+ and CD8+ PSIs provided the overall PSI index for each sample. A monofunctional strength index, or MSI metric, defined as the percentage of monofunctional cells multiplied by the secretion intensity of that cytokine was also calculated.

Any notable statistically significant associations between the pre-infusion single-cell CAR T data and clinical outcome were determined, cognizant of the clinical outcome of these patients (objective response, CRS, and NT). More specifically, associations between overall PSI, CD4+ PSI, CD8+ PSI, IL-17A CD4+ PSI, and clinical outcomes were determined. Mann Whitney U tests were used to determine P values of these associations. Moreover, any associations between these single-cell metrics (e.g., PSI) and other pre- and post-infusion metrics described throughout this paper (e.g., in vivo CAR T cell expansion, IL-15 day 0 patient levels, co-culture and serum cytokine levels, T cell phenotype frequencies) were determined by measuring the Spearman correlation between these metrics.

Figure 6A:
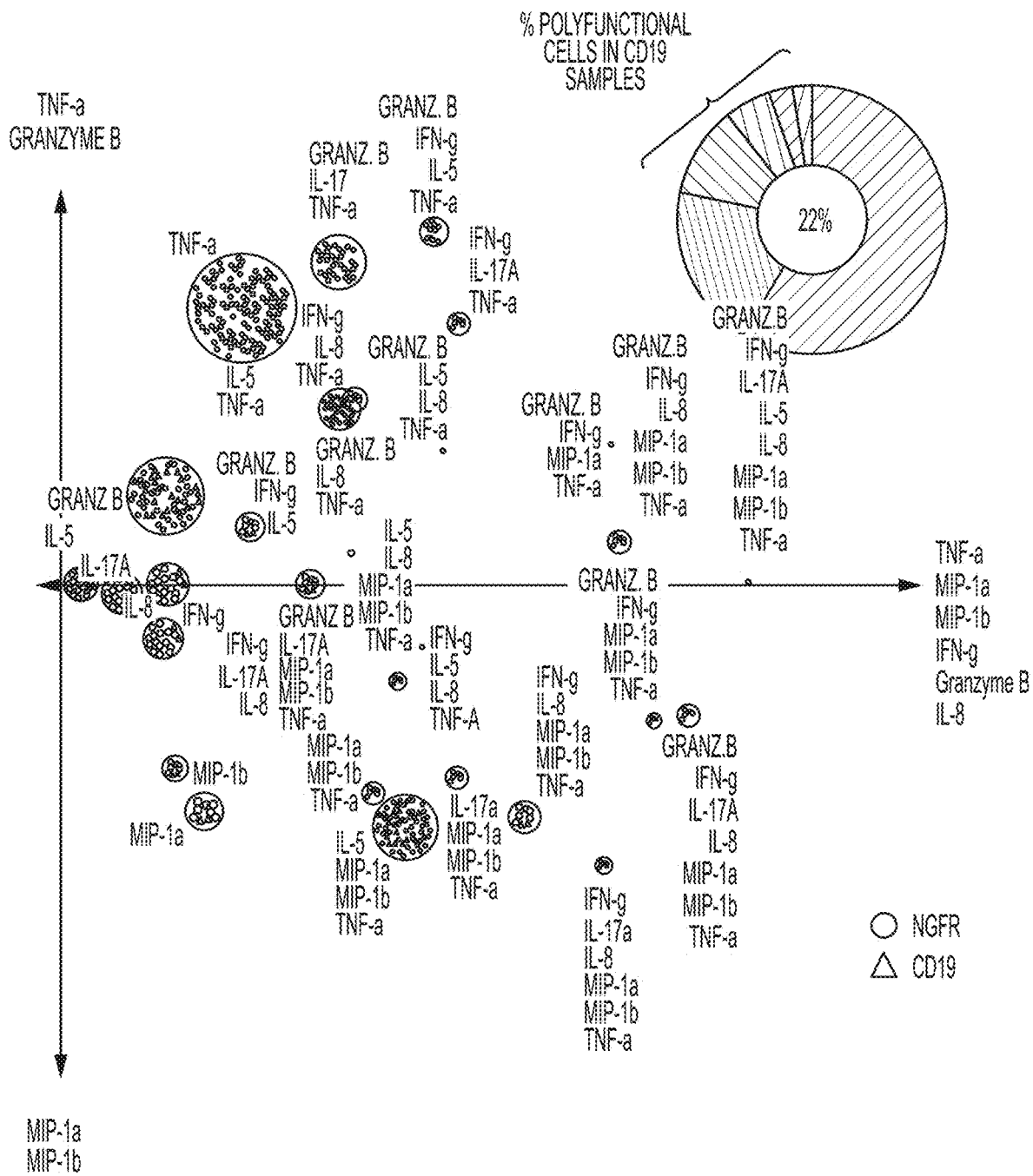
FIGS. 6A-6B show polyfunctional CD4+ and CD8+ T cell subpopulations defined by single-cell analysis. The functional subsets were determined by principal component analysis within CD4+(FIG. 6A) and CD8+(FIG. 6B) T cell subsets. The representation is based on clustering cytokines produced by individual cells as 2-D representation of objects in multidimensional space. The major polyfunctional subsets defined by similarity of the cytokines produced are represented as clusters, with individual dots corresponding to cells. The intensity of the dot reflects the cytokine production level. The major cytokines that are most commonly represented within each major population, CD4 and CD8 T cells respectively, have been used to organize this principal component analysis (indicated on x and y axis) and the cytokines defining each cluster are indicated. The frequency of polyfunctional cells, comprising about 20-25% of all immunologically relevant cells, is also represented.
Figure 6B:
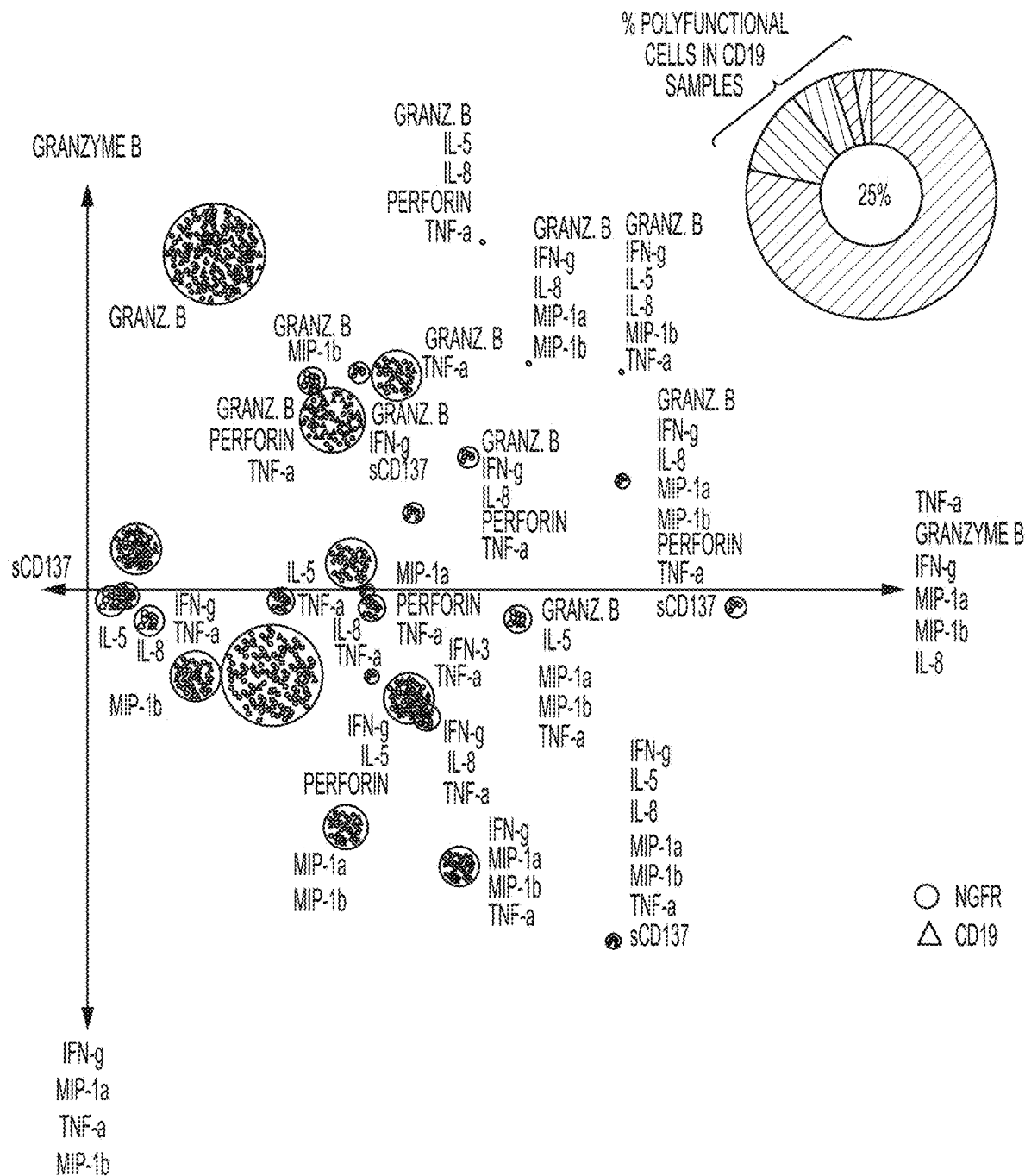

The polyfunctional profiles of CAR product T cells stimulated with CD19+ cells were dominated by effector molecules, stimulatory/proliferative cytokines, and chemokines. Detailed evaluation including principal component analysis (PCA) showed a complex and heterogeneous functional profile of product T cells, with both polyfunctional CD4+ and CD8+ T cell subsets secreting predominantly IFN-γ, IL-8, IL-5, Granzyme B and/or (macrophage inflammatory protein) MIP-1α (FIGS. 6A, and 6B). Notably, the CD4+ but not CD8+ T cell population also contained IL-17A+ polyfunctional T cells.

As shown in FIGS. 6A and 6B, functional subsets were determined by principal component analysis, within CD4+ and CD8+ product T cell subsets. The representation is based on clustering utilizing cytokines produced by individual cells, as 2-dimensional representation of objects in multidimensional space. The major polyfunctional subsets defined by similarity in the cytokines produced are represented as clusters with individual dots corresponding to cells. The intensity of dots reflects the cytokine production level. The polyfunctionality of the T cell population not stimulated with CD19+ cells is overlaid (blue color, NGFR) as a control. The major cytokines that are most commonly represented within each major population, CD4 and CD8 T cells respectively, have been used to organize this principal component analysis (indicated on x and y axis) and the cytokines defining each cluster are indicated. The frequency of polyfunctional cells, comprising only about 20-25% of all immunologically relevant cells, is also represented.

Figure 1A:
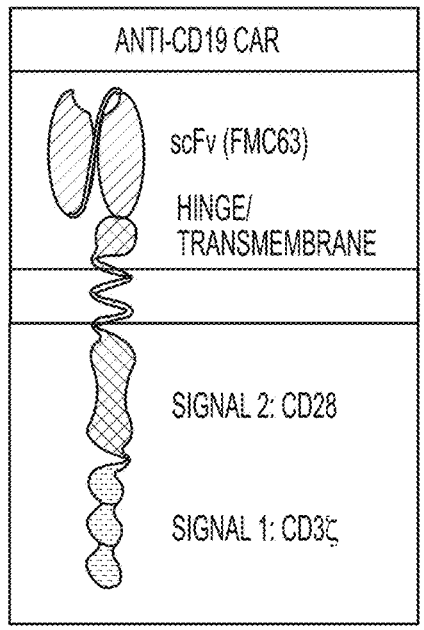
FIGS. 1A-1F show a schematic representation of the method used to evaluate T cell polyfunctionality.
Figure 1B:
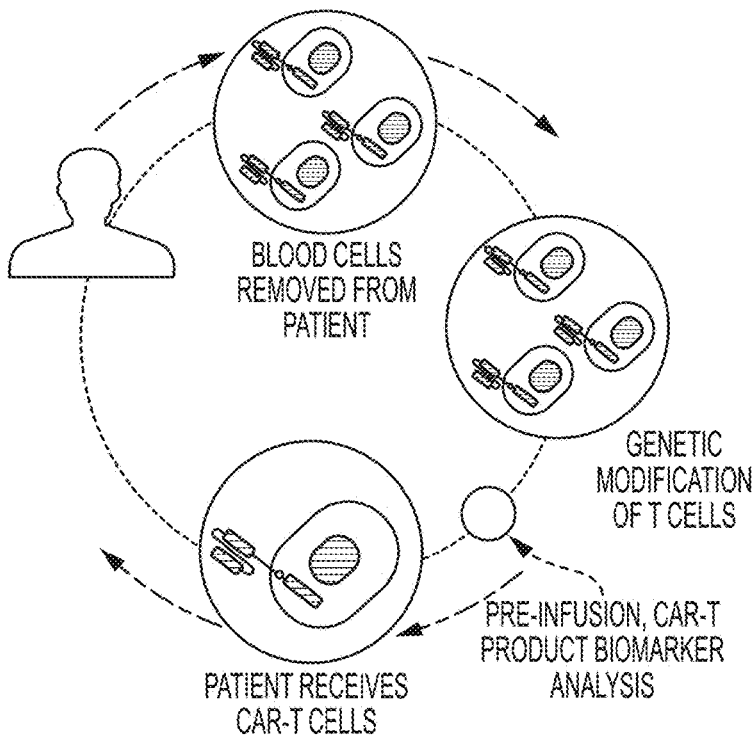
Figure 1C:
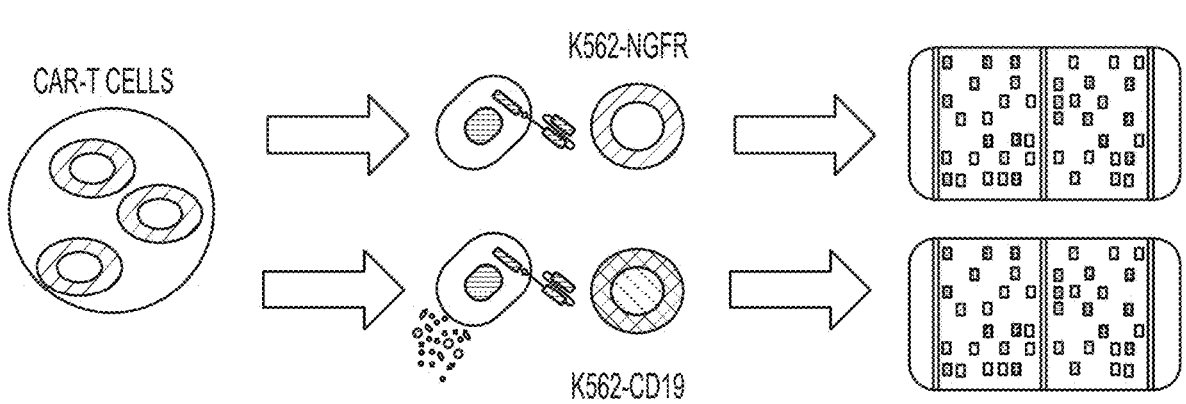
Figure 1D:
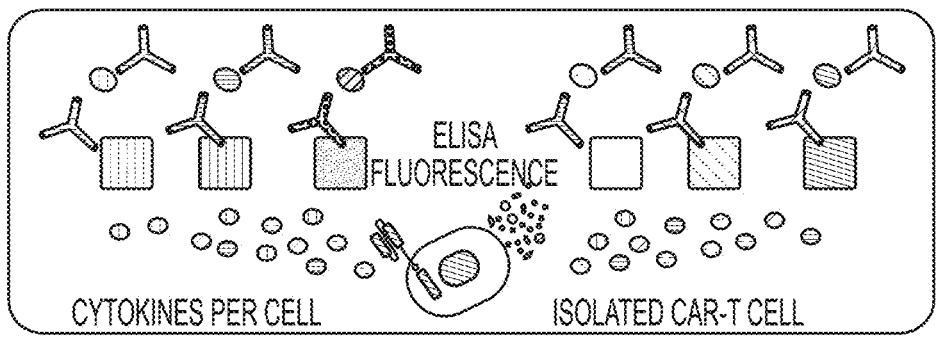
Figure 1E:
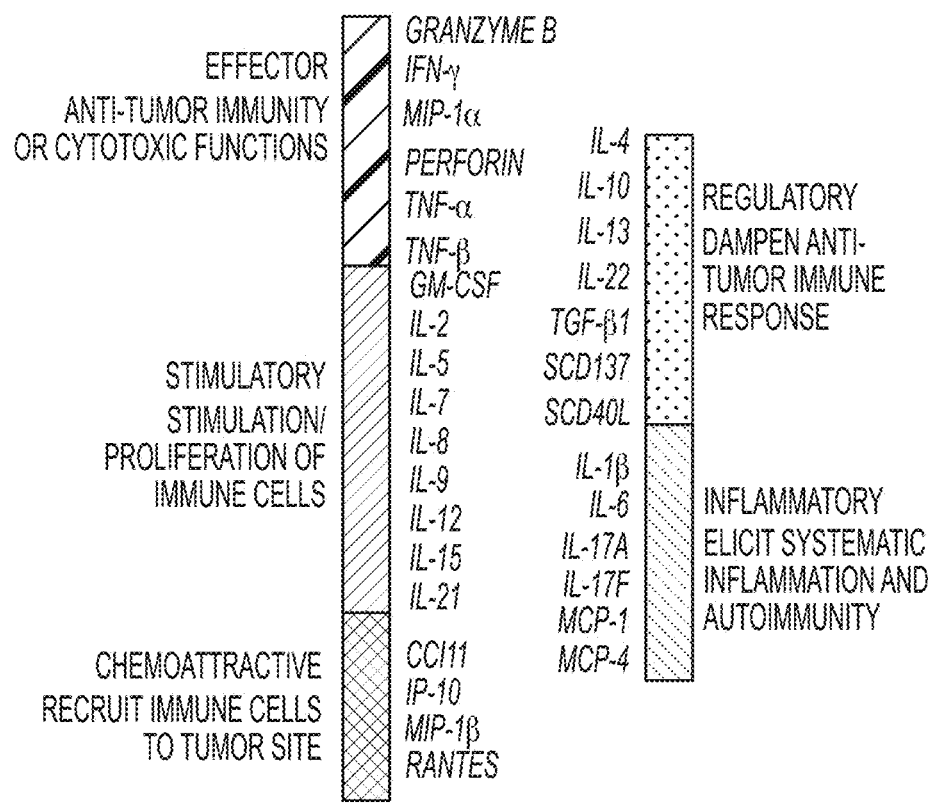
Figure 1F:
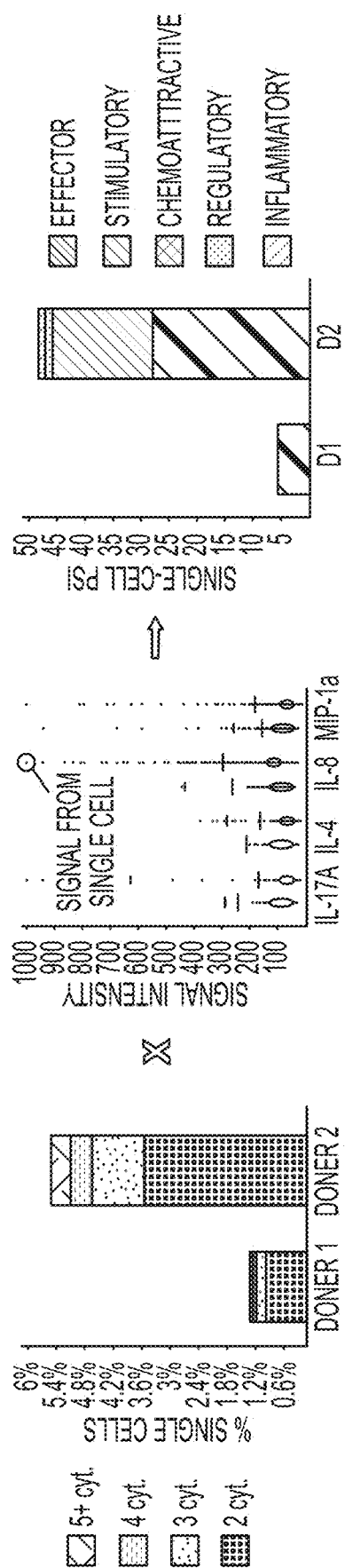
Figure 2A:
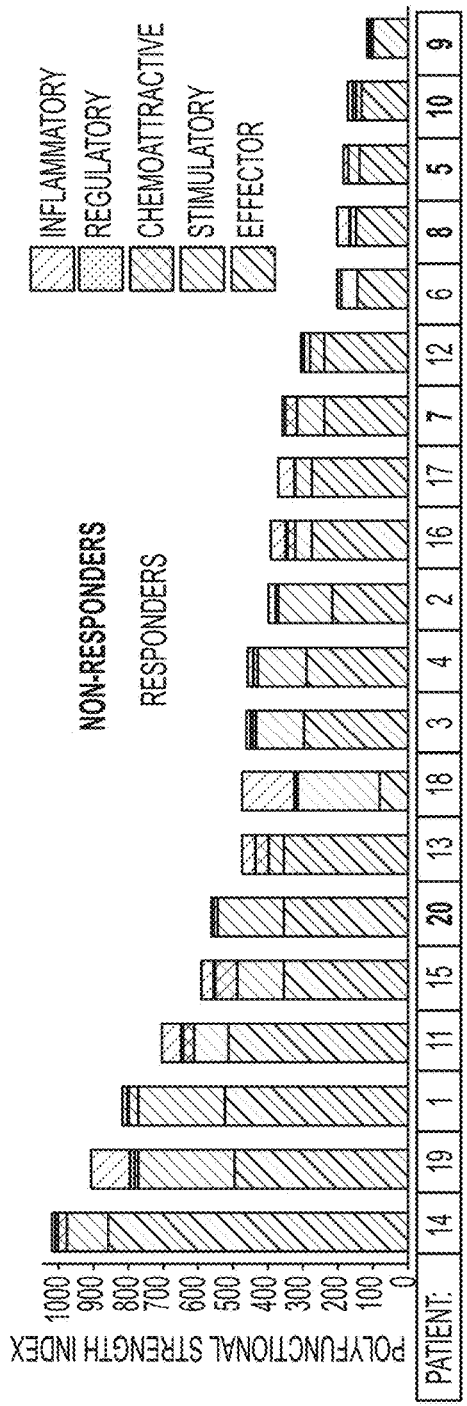
FIGS. 2A-2D show association of PSI with objective response (OR), and treatment-related adverse events (AEs). Single-cell product PSI was determined for 20 patient donors, by using SCBC proteomics analysis of a panel of 32 secreted cytokines, chemokines, and cytotoxic molecules. The products were ranked according to CAR T cell PSI levels and the PSI was associated with the OR (FIG. 2A, 2C), or grade 3+ CRS (FIG. 2B, 2D) as indicated. The results are shown as patient-level PSI (FIG. 2A, 2B) and mean±SE PSI (FIG. 2C, 2D). All statistical values were computed using the Mann Whitney U Test. AE, adverse event; CRS, cytokine release syndrome; OR, objective response; SCBC, single-cell barcode chip; SE, standard error.
Figure 2B:
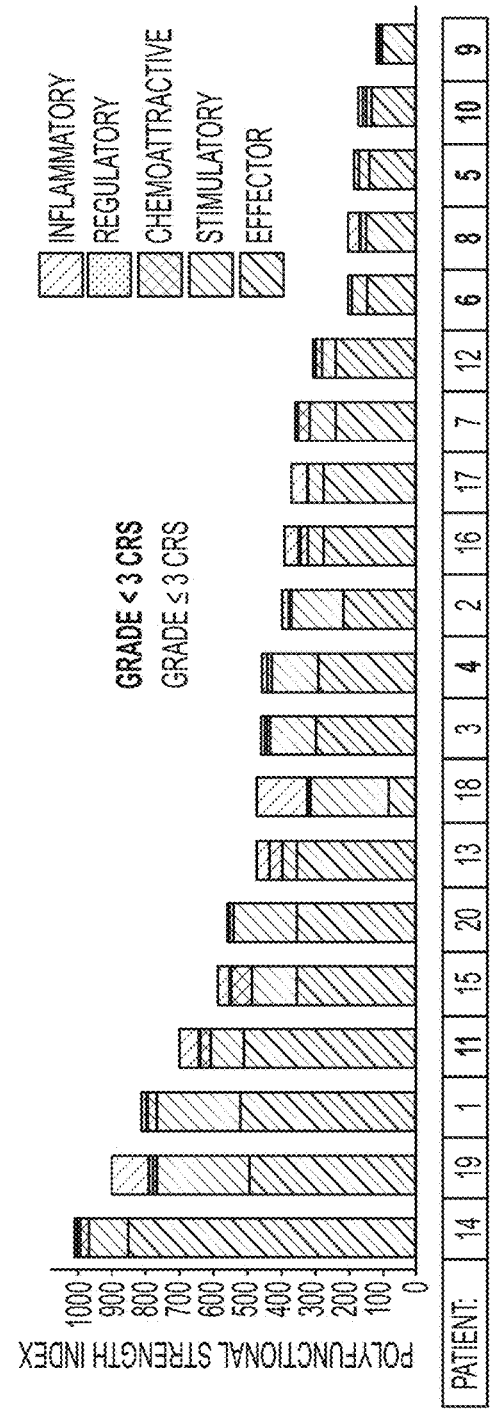
Figure 2D:
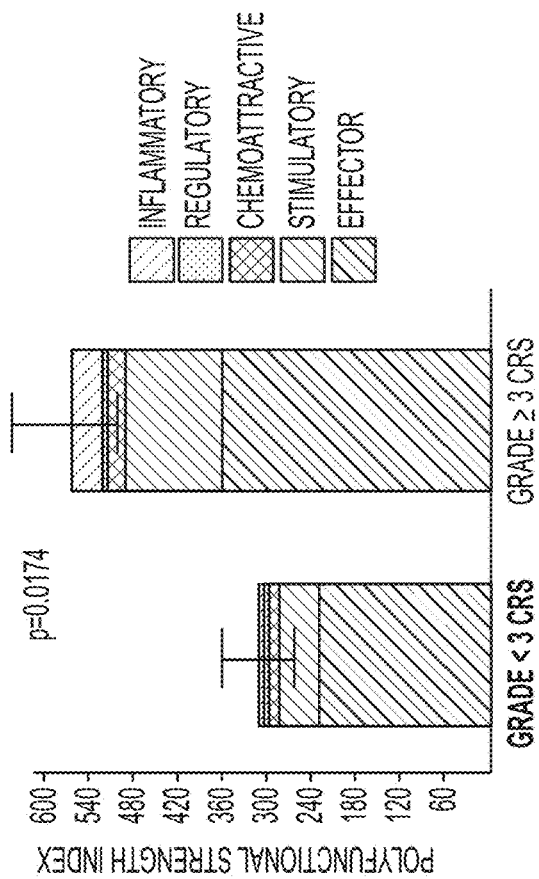
Figure 2C:
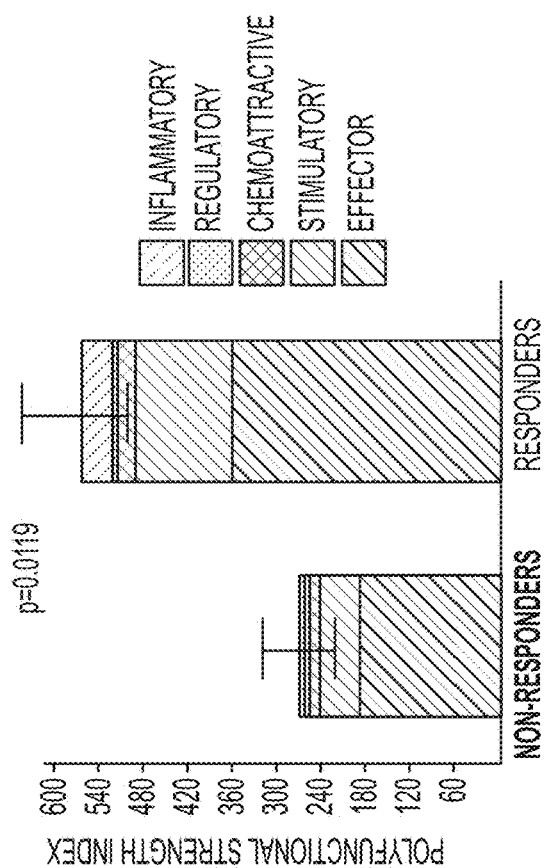
Figure 3A:
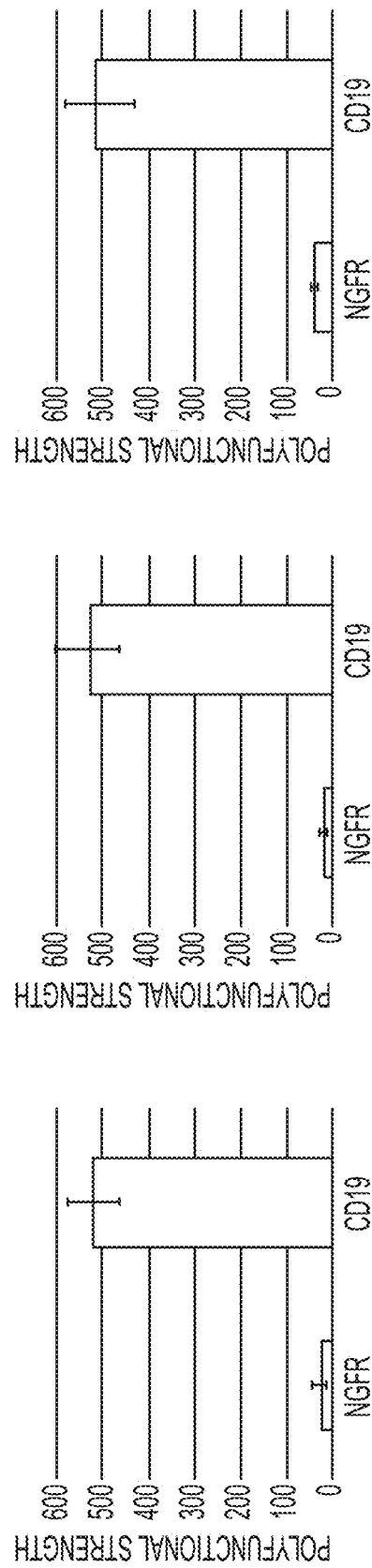
Figure 3E:
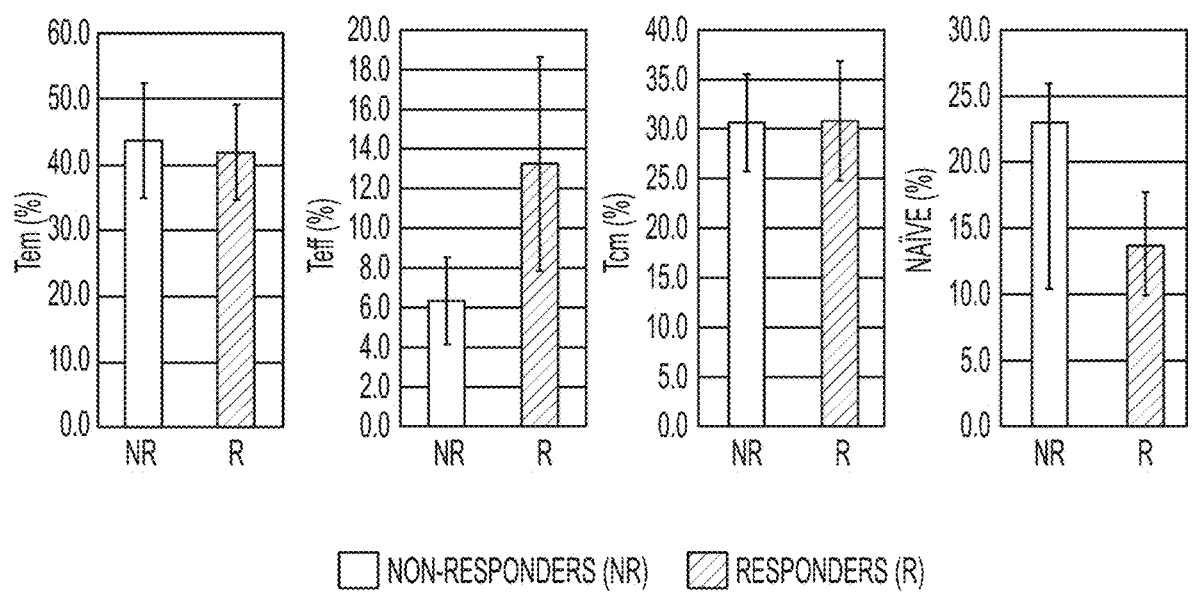
Figure 3F:
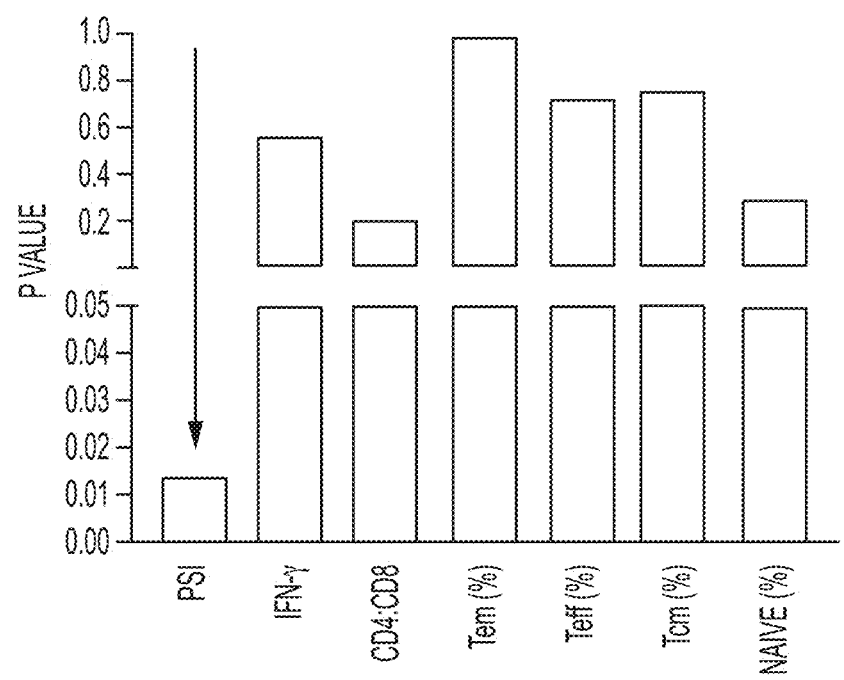
Figure 4A:
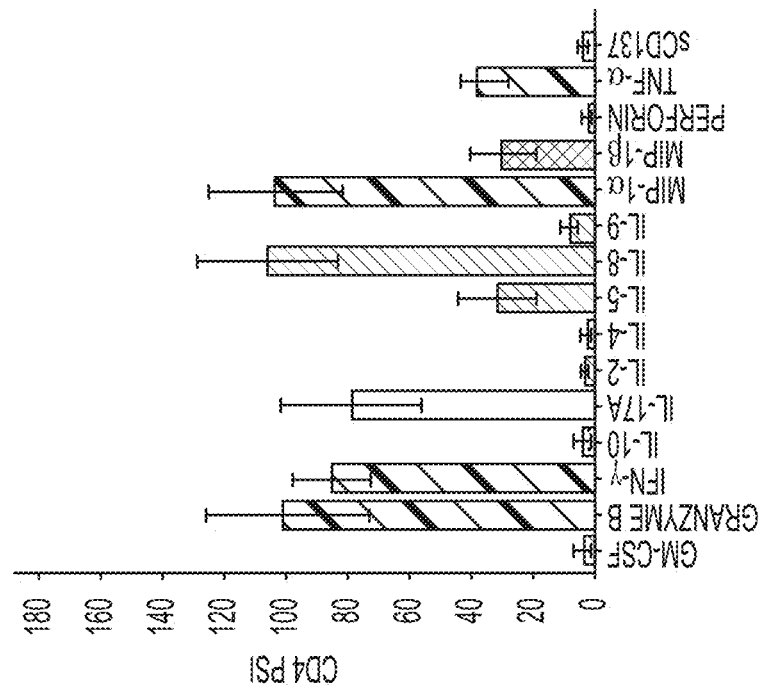
FIGS. 4A-4D show major cytokines driving polyfunctional product CD4+ and CD8+ T cells by CD19 stimulation that distinguish responders (R) to the therapy from nonresponders (NR).
Figure 4A:
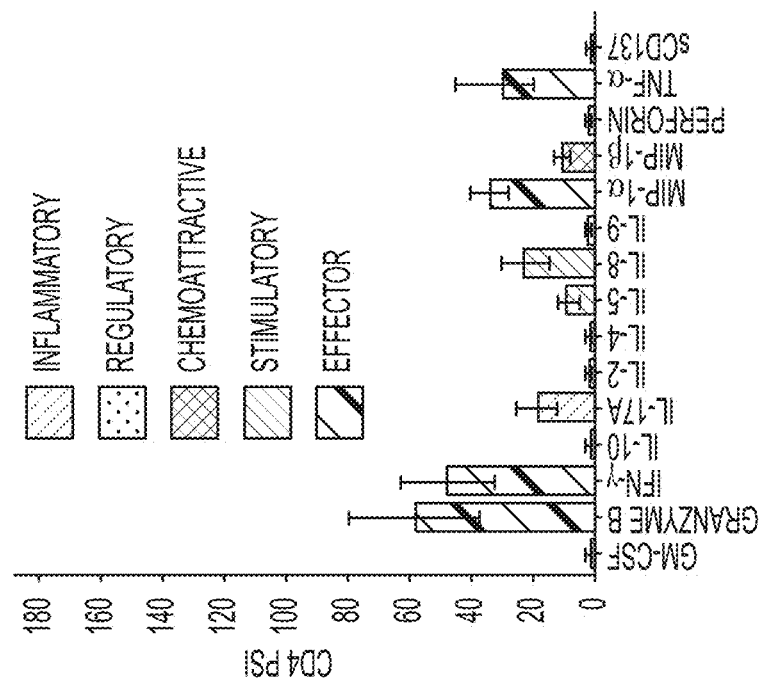
Figure 4B:
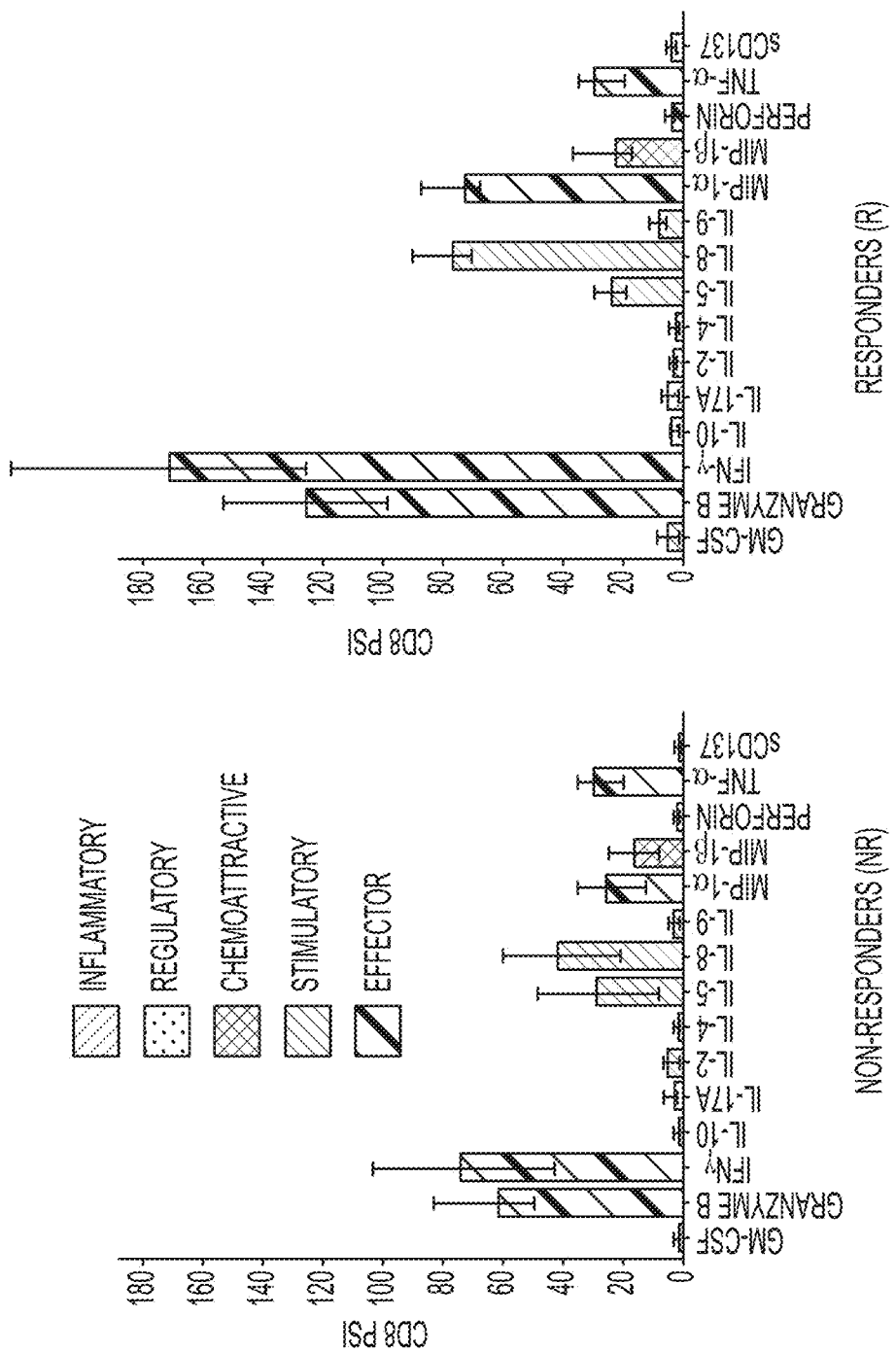
Figure 4C:
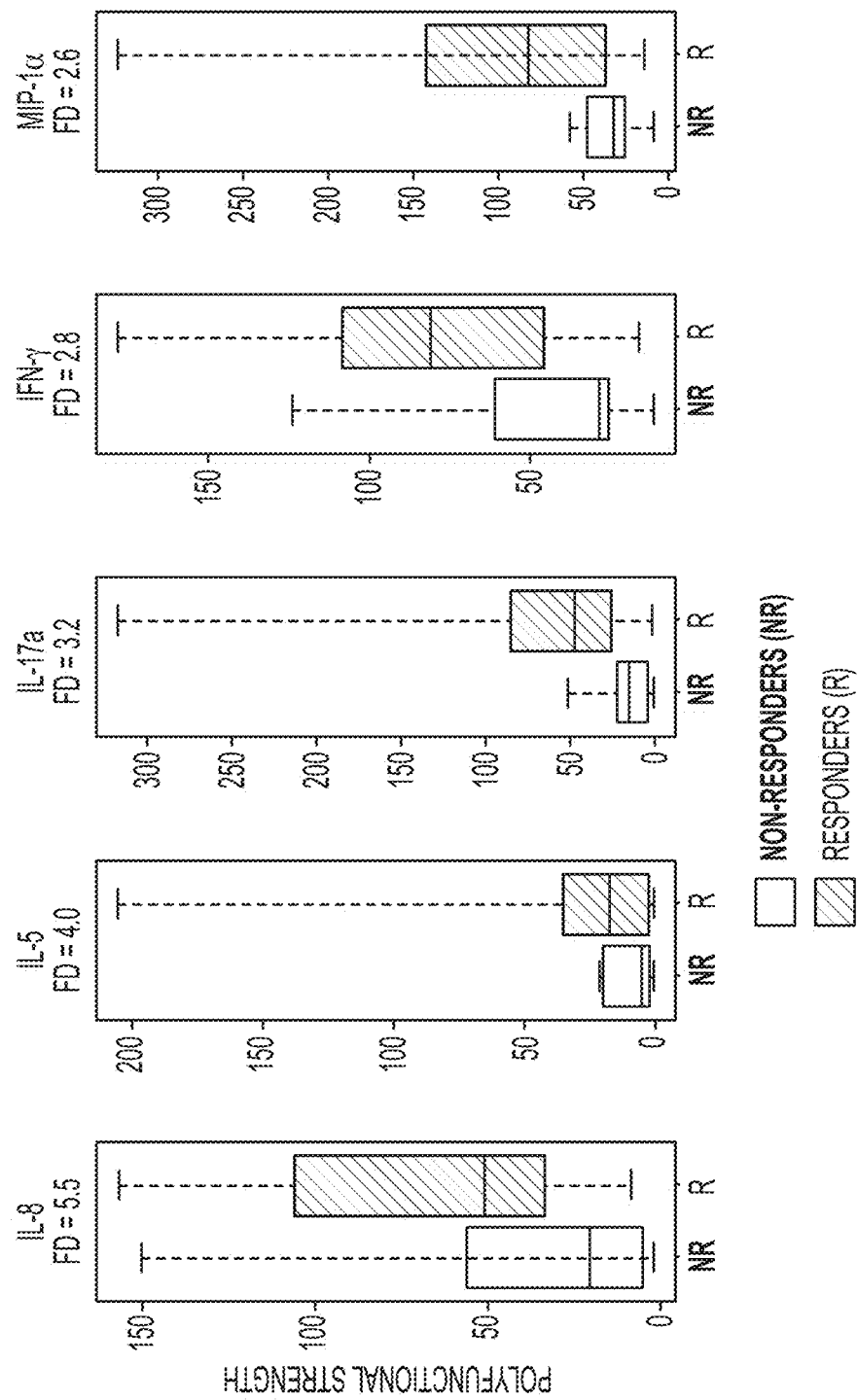
Figure 4D:
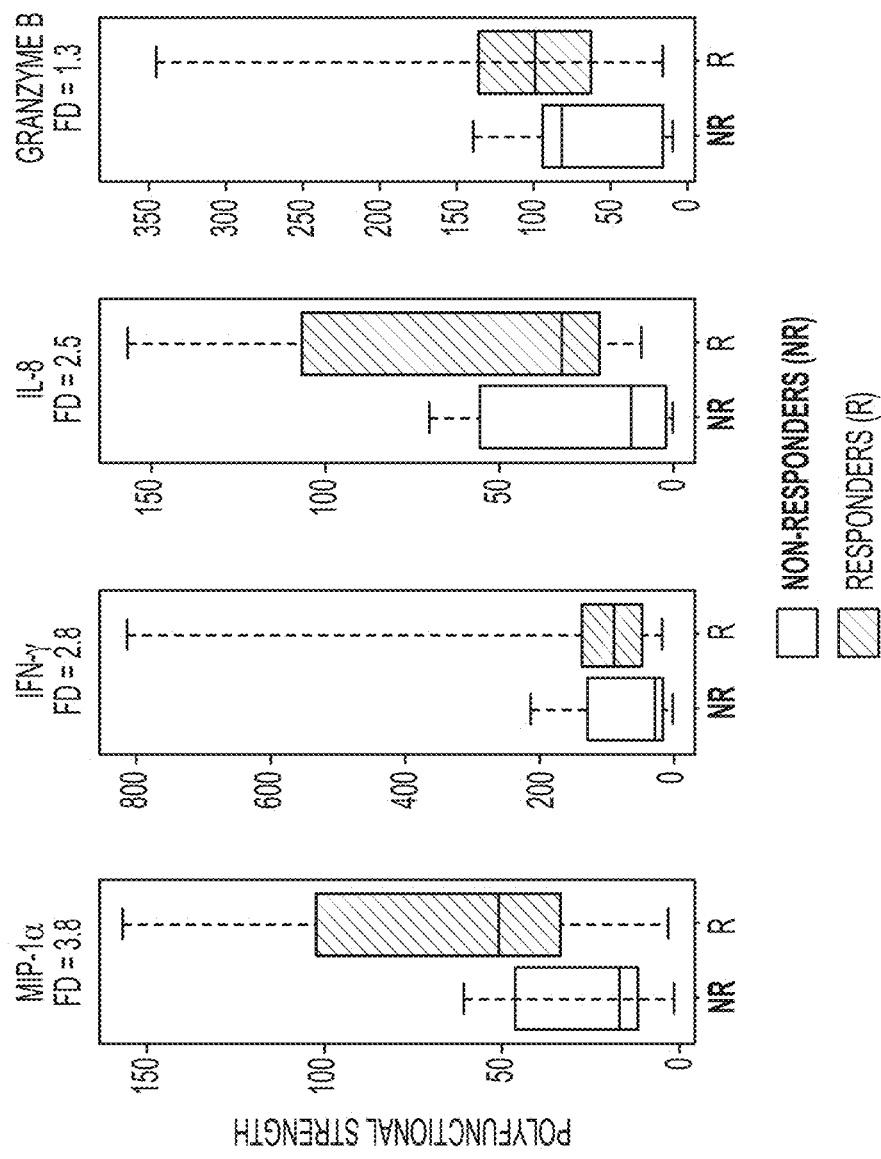

Overall, products displayed a wide range of PSI values; the polyfunctional cells comprised only 20-25% of all cytokine-producing product T cells. Global product PSI was significantly associated with OR (P=0.0119; FIG. 2C). The median PSI was twice as high for responders versus non-responders. Higher product PSI was also statistically associated with grade 3+ cytokine release syndrome (CRS; P=0.0174; FIG. 2D). In contrast to PSI findings, a similarly computed index corresponding to monofunctional T cells in the product did not have associations with OR, grade 3+NT, or grade 3+ CRS (data not shown). Major product phenotypes defined by flow cytometry and IFNγ in co-culture were not associated with clinical response (FIGS. 3A-3F).

The major cytokines and chemokines produced by product polyfunctional T cells in the responding patients comprised IFNγ, MIP-1a, IL-8 in both CD4 and CD8 T cells, Granzyme B in CD8 T cells and IL-17A and IL-5 in CD4 T cells (FIGS. 4A-4D).

Surprisingly, these results suggest that the combination of frequency and cytokine production levels of polyfunctional T cells in product, associate with the clinical response and toxicity to treatment with CAR T cells.

Measurement of In Vivo CAR T Cell Levels

CAR T cell expansion in blood was measured by qPCR. For each patient, DNA was extracted from peripheral blood mononuclear cells (PBMC) collected before treatment and at multiple time points after treatment. DNA was extracted using a Qiagen DNeasy blood and tissue kit (Qiagen, Hilden, Germany). DNA from each time point was amplified in duplicate with a primer and probe set (Applied Biosystems, Foster City, Calif.) that was specific for the CAR. Real-time PCR was carried out with a Roche Light Cycler 480 real-time PCR system (Roche Diagnostics Corp, Indianapolis, Ind.). Serial 1:5 dilutions of DNA were made from the infused T cells of each patient into pretreatment DNA from the same patient, and standard curves were made by performing qPCR on this DNA.

Measurement of Cytokines in Co-Culture and Serum by Multiplex Analysis

Co-culture experiments were performed using K562 cells engineered to express CD19 or NGFR (negative control) mixed 1:1 with CAR T cell product. Cell culture medium was harvested 24 hours post-incubation for subsequent analysis. Thirty-one analytes were evaluated by Meso Scale Discovery (MSD®; Rockville, Md.), MULTI-SPOT®, and EMD Millipore (Burlington, Mass.) Luminex® xMAP® multiplex assays. Serum IL-15 was measured using EMD Millipore Luminex® xMAP® multiplex assays. Data acquisition and analysis were performed using a Luminex 200™ instrument and xPONENT® 3.1 data analysis software.

Evaluation of Percentage of T17 and Treg Cells by Epigenetic Analysis

Epigenetic analysis was performed based on previously characterized methods (Baron, U. et al. DNA demethylation in the human FOXP3 locus discriminates regulatory T cells from activated FOXP3(+) conventional T cells. Eur J Immunol 37, 2378-2389 (2007)). Genomic DNA was isolated using the DNeasy tissue kit (Qiagen) following the protocol for cultured animal cells. Bisulfite treatment of genomic DNA was performed. PCR was performed in a final volume of 25 μL containing 1×PCR Buffer, 1 U Taq DNA polymerase (Qiagen), 200 μmol/L dNTP, 12.5 pmol each of forward and reverse primers, and 7 ng bisulfite-treated genomic DNA at 95° C. for 15 min, and 40 cycles of 95° C. for 1 min, 55° C. for 45 s and 72° C. for 1 min, and a final extension step of 10 min at 72° C. PCR products were purified using ExoSAP-IT (USB Corp, Cleveland, Ohio) and sequenced by applying the PCR primers and the ABI Big Dye Terminator v1.1-chemistry (Applied Biosystems) followed by capillary electrophoresis on an ABI 3100 genetic analyzer. ESME was used to interpret AB1 files.

Determination of Product T Cell Phenotypes by Flow Cytometry

For CD4, CD8, and central memory phenotype were determined by flow cytometry. (Kochenderfer, et al. B-cell depletion and remissions of malignancy along with cytokine-associated toxicity in a clinical trial of anti-CD19 chimeric-antigen-receptor-transduced T cells. Blood 119, 2709-20 (2012)). CAR+CD3+ events were gated and the percentage of cells expressing memory markers CCR7 and CD45RA was determined. Appropriate isotype control antibodies were used in all experiments. The memory antibodies used were anti-CD45RA (eBioscience, San Diego, Calif. clone HI100) and anti-CCR7 (R&D Systems clone 150503).

Gene Expression Analysis

Cryopreserved then thawed cells were enumerated using a Vi-CELL automated cell counter (Beckman Coulter, Brea, Calif.). Live cell suspensions were used as input into the NanoString Vantage 3D RNA:Protein Immune Cell Profiling Panel (Seattle, Wash.), which is a 770-plex gene and 30-plex protein expression panel that profiles the human immune response. For CD19-K562 or NGFR-K562 samples, 50,000 cells were used for RNA and 100,000 cells for protein. For K562 plus CAR T cell co-cultures, 150,000 cells were used for RNA and 200,000 cells for protein. For CAR T cells, 300,000 cells were used for RNA and 200,000 cells for protein. A custom gene expression panel of 191 additional immune and metabolic-related markers, including probes specific for the anti-CD19 CAR, was also run on the cell lysates made for the RNA:Protein assay. Raw data were imported from the MAX digital analyzer into nSolver software v3.0. Standard quality control checks assessing imaging, binding density, positive control linearity, and limit of detection were performed. By utilizing the internal positive controls in the panels, raw gene and protein expression data were first normalized. Then, the mRNA data were further normalized by the geometric mean of a set of stably expressed reference genes, and the protein data were normalized by the geometric mean of a set of stably expressed proteins. The mRNAs and proteins expressed below background were filtered from the analysis using cutoffs of mean+2 standard deviations (SD) of negative controls (for mRNA), and 3× geometric mean of immunoglobulin G-negative controls (for protein).

Example 2: Combined Indexes of Product PSI and CAR T Cell Expansion or Pre-CAR T Cell Infusion Levels of IL-15, Correlated Strongly with Clinical Response and Toxicities After infusion, CAR T cells rapidly expand, with peak levels occurring within the first 7-14 days. CAR T cell expansion measured as peak and cumulative levels during the first month after infusion is associated with OR and grade 3+NT, but not grade 3+ CRS.

Combined indices of PSI with either peak CAR T-cell levels in blood, or with day 0 IL-15 serum levels, had significant associations with clinical outcomes versus either parameter alone. Day 0 IL-15 serum levels, elevated by conditioning chemotherapy, were measured just before CAR T-cell infusion. OR was associated with both CD4+ PSI plus day 0 IL-15, as well as IL-17A PSI plus day 0 IL-15. The combined index was computed by adding the 2 metrics to each other, after first standardizing them to have comparable variances. This standardization was achieved by dividing the metrics by their respective standard deviation to bring them to a common magnitude/scale.

Figure 7A:
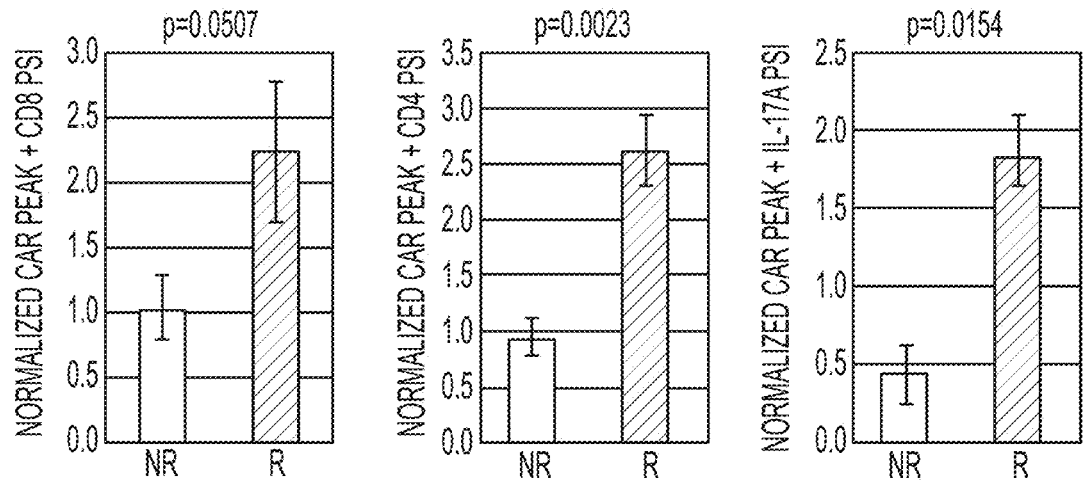
FIGS. 7A-7B show association between PSI in conjunction with CAR T cell levels in blood and objective response (.
Figure 7B:
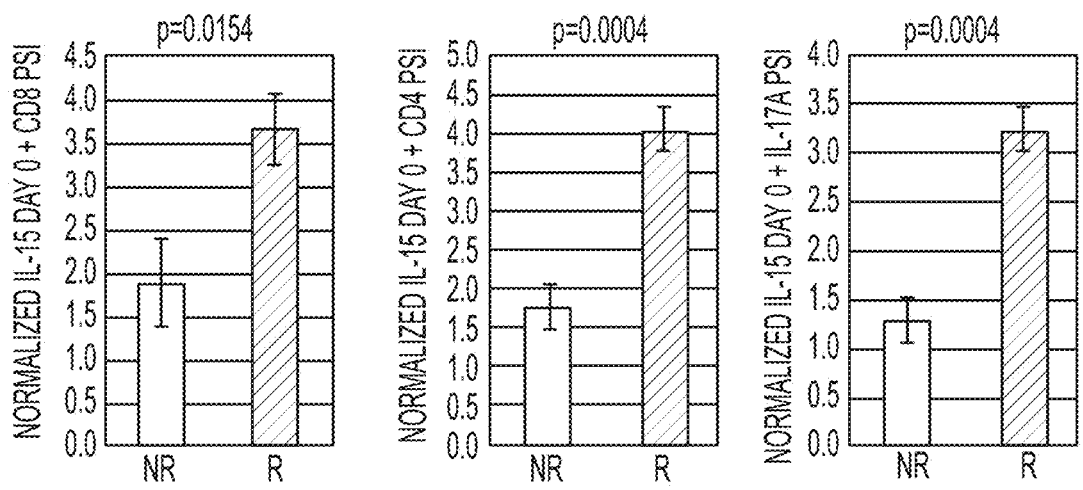

This composite index combining PSI and CAR T cell expansion improved the association with OR (P=0.0046, not adjusted for multiplicity) compared with each co-variate alone (FIGS. 5A-5E). Furthermore, OR associated with CD4+ PSI plus CAR peak levels (P=0.0023), but only marginally with CD8+ PSI plus CAR peak levels, respectively (P=0.0507; FIGS. 7A and 7B). As shown in FIGS. 7A and 7B, association between PSI in conjunction with CAR T cell levels in blood, or day 0 IL-15 levels in serum, and objective response. CAR T cell levels in blood were measured by qPCR. A composite index integrating PSI and CAR T cell expansion in vivo was developed and associated with response outcome (R=response; N=no response). Whole-product PSI, CD4+ PSI, and IL-17A PSI indexes were all evaluated in conjunction with CAR peak levels. The 2 metrics were combined into a joint metric to test their association with a patient outcome. The metrics were added to each other after first standardizing each of them to have unit variance. This standardization was achieved by dividing the metric by their respective standard deviation to bring them to a common magnitude/scale. Joint PSI and day 0 IL-15 level metrics were calculated similarly. Statistical values were computed using the Mann Whitney U test. P values were not adjusted for multiplicity.

Figure 8:
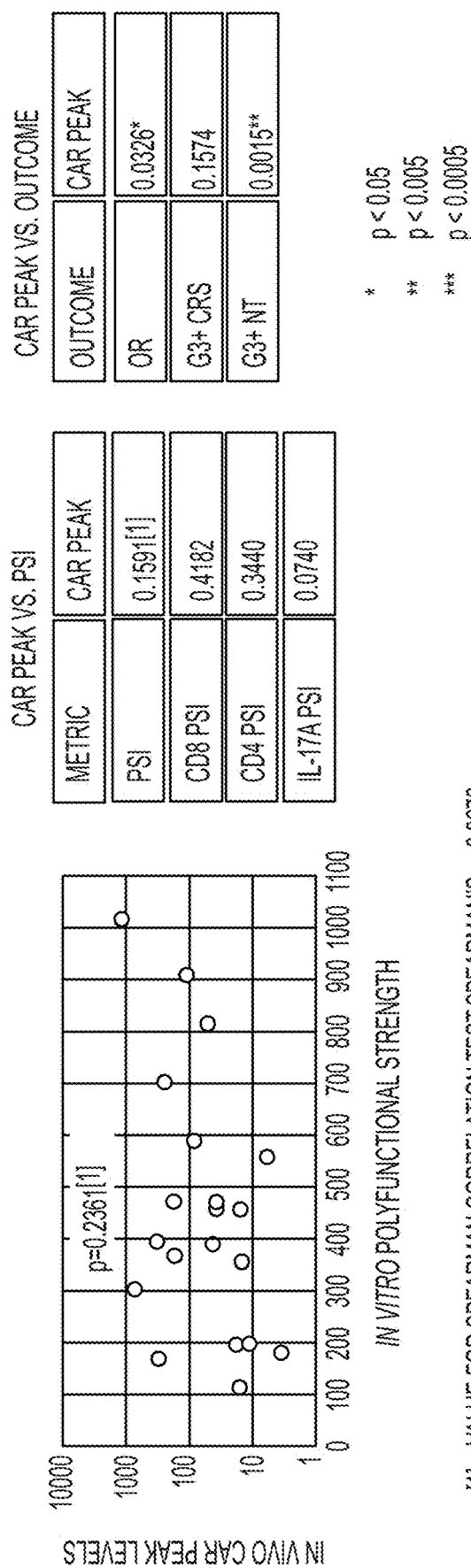
FIG. 8 shows PSI does not associate with CAR T cell levels in blood. CAR T cell levels in blood were measured by qPCR and correlated with PSI or clinical outcome (OR, grade 3+NE or CRS). Whole-product PSI, CD4+ PSI, and IL-17A PSI are displayed. Statistical analysis was performed using Spearman's correlation and Mann Whitney U tests.
Figure 9A:
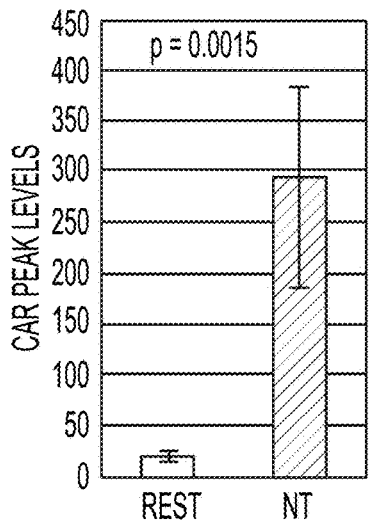
FIGS. 9A-9F show association between PSI in conjunction with CAR T cell levels in blood, and grade 3+ neurologic toxicity (NT). CAR T cell levels in blood were measured by qPCR and correlated with grade 3+ adverse events. A composite index integrating PSI and CAR T cell expansion in vivo was developed and associated with NT or CRS, respectively. Statistical values were computed using the Mann Whitney U test. P values were not adjusted for multiplicity.
Figure 9B:
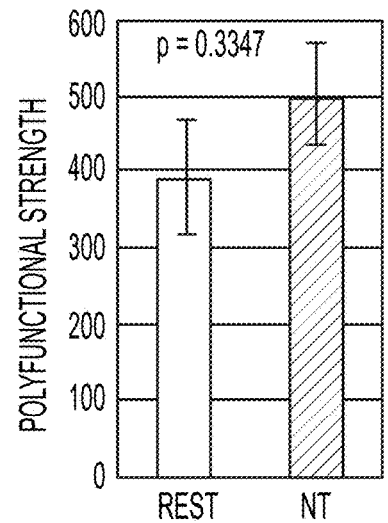
Figure 9C:
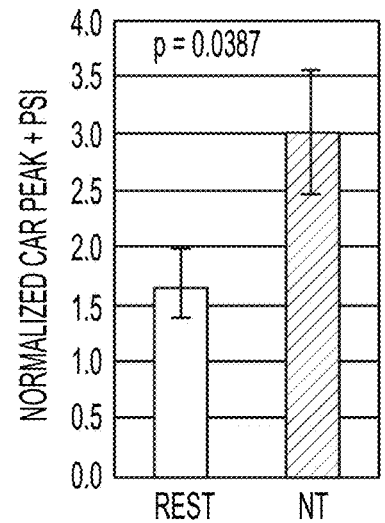
Figure 9D:
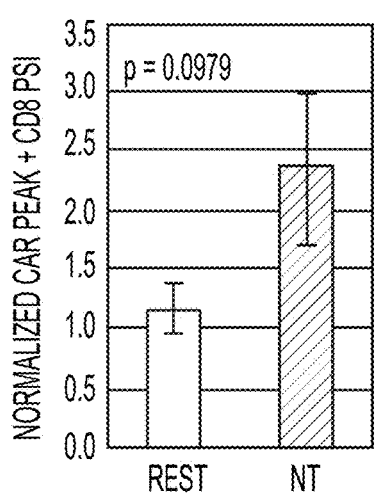
Figure 9E:
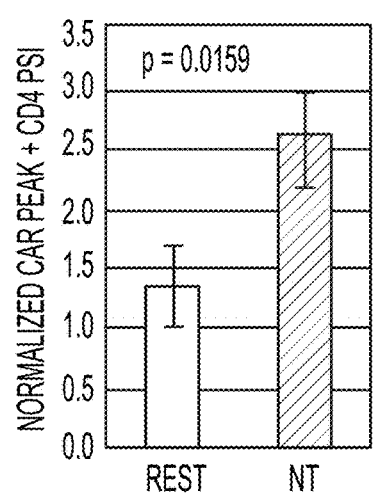
Figure 9F:
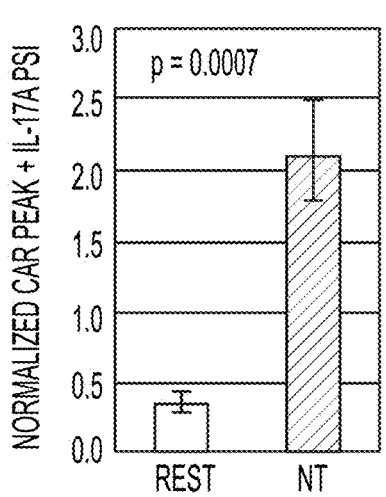
Figure 10A:
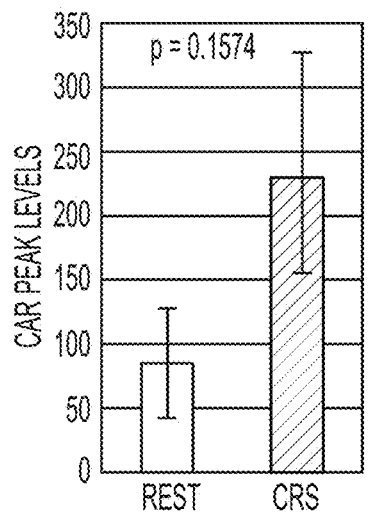
FIGS. 10A-10F show association between PSI in conjunction with CAR T cell levels in blood, and grade 3+ cytokine release syndrome (CRS). CAR T cell levels in blood were measured by qPCR and correlated with grade 3+ adverse events. A composite index integrating PSI and CAR T cell expansion in vivo was developed and associated with NE or CRS, respectively. Whole-product PSI, CD4+ PSI, and IL-17A PSI indexes were all evaluated in conjunction with CAR peak levels. Statistical values were computed using the Mann Whitney U test. P values were not adjusted for multiplicity.
Figure 10B:
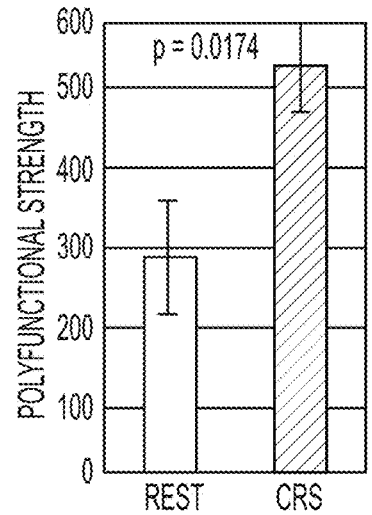
Figure 10C:
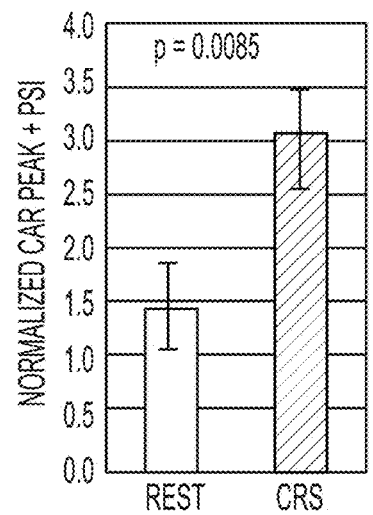
Figure 10D:
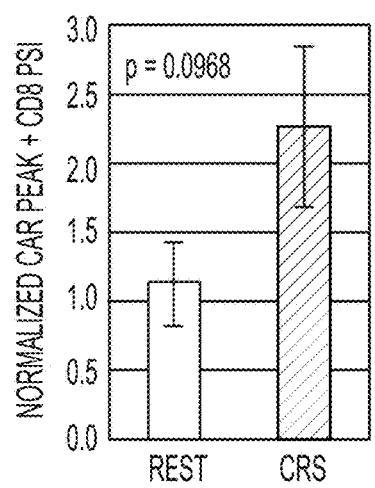
Figure 10E:
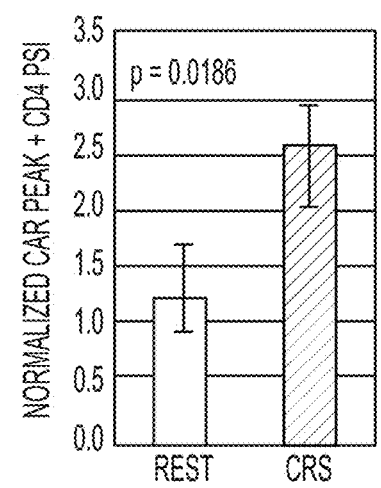
Figure 10F:
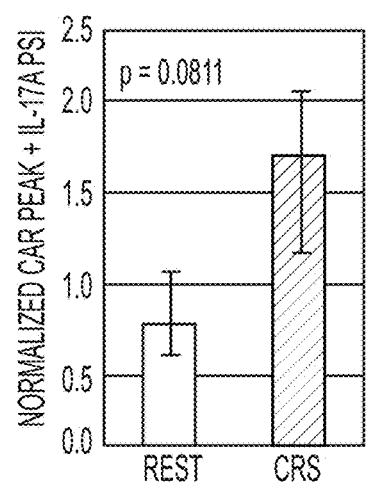
Figure 11A:
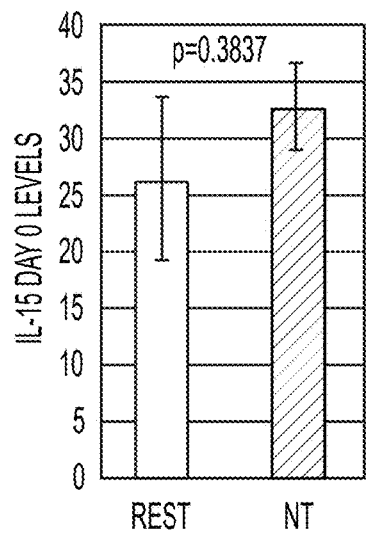
Figure 11B:
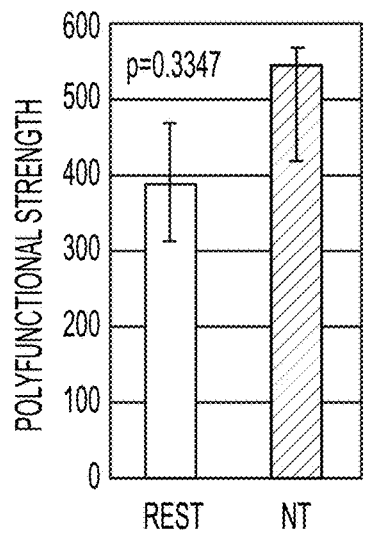
Figure 11C:
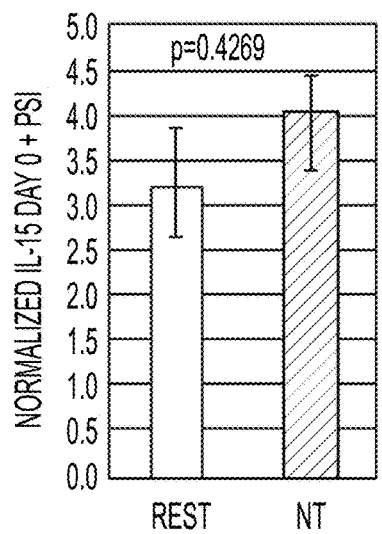
Figure 11D:
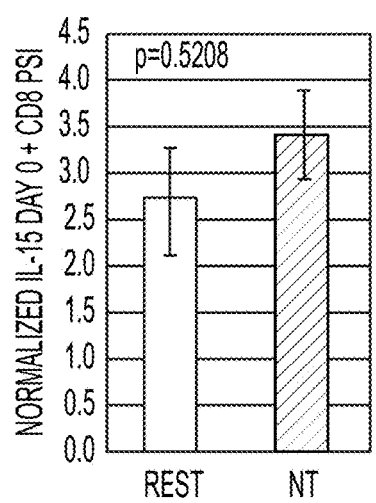
Figure 11E:
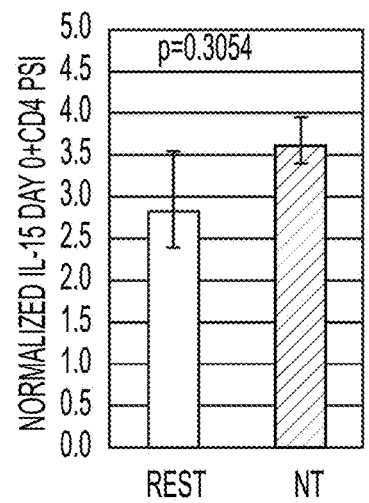
Figure 11F:
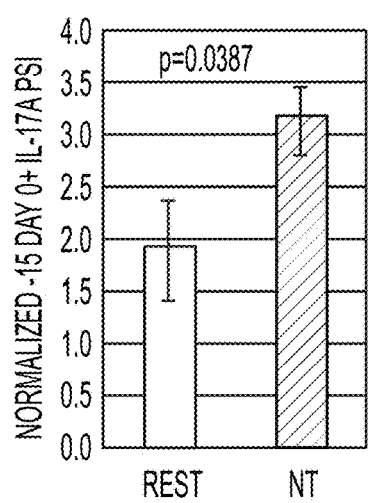
Figure 12A:
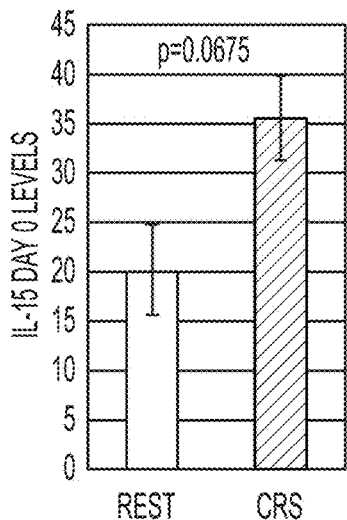
Figure 12B:
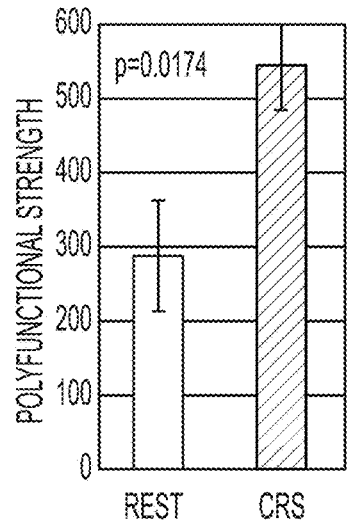
Figure 12C:
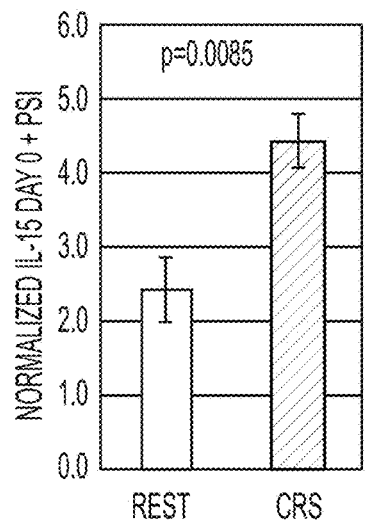
Figure 12D:
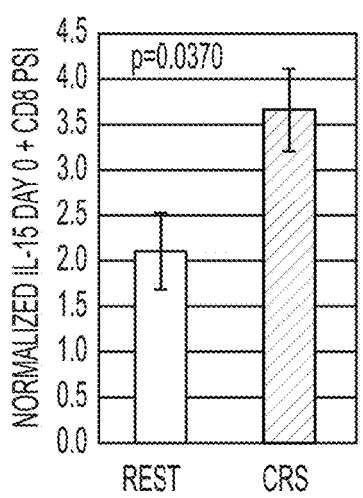
Figure 12E:
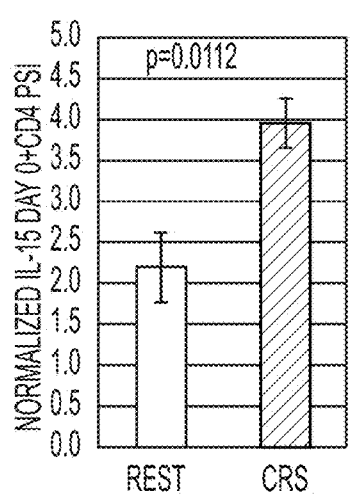
Figure 12F:
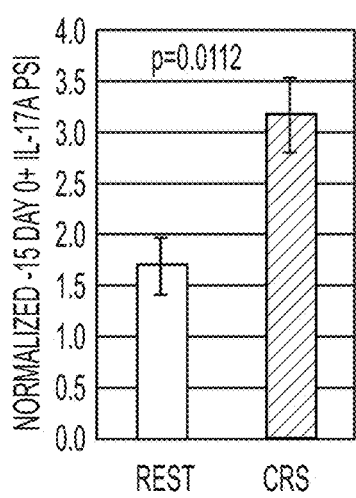

As shown in FIG. 8, there was no apparent association between CAR peak levels and PSI (FIG. 8). PSI does not associate with CAR T cell levels in blood. CAR T cell levels in blood were measured by qPCR and correlated with PSI or clinical outcome (OR, grade 3+NE or CRS). Whole-product PSI, CD4+ PSI, and IL-17A PSI are displayed. Statistical analysis was performed using Spearman's correlation and Mann Whitney U tests.

PSI was not significantly associated with commonly assessed product phenotypes based on CCR7 and CD45RA expression (FIG. 3A-3F). CAR gene expression levels were measured by nanostring in bulk product together with T cell housekeeping molecules. Global PSI was found to be associated with the ratio between CAR mRNA copies and T cell-specific markers (Table 2). This finding suggests that the level of CAR expression in the product associate with product T cell polyfunctionality.

Table 2 shows associations between PSI and ratio of CAR gene expression/T cell related molecules, all measured quantitatively by nanostring. CAR gene expression was measured utilizing probes for CD28 CD3zeta junction and scFv, respectively. T cell related mRNA was measured utilizing probes for CD3D, CD3E, CD3G and CD6. CD3E was also measured at protein level using anti-CD3 mAb OKT3, by nanostring. PSI was also analyzed against T cell molecules alone. The analysis was done by linear regression. * P<0.05. ** P<0.005.

TABLE 2

Product Gene Expression Correlations with PSI.

| PSI vs. | Alone | Ratio vs. CD28_CD3z | Ratio vs. scFv |
|---|---|---|---|
| CD3D | 0.9925 | 0.0077* | 0.0141* |
| CD3E | 0.7122 | 0.0029** | 0.0052* |
| CD3G | 0.7051 | 0.0096* | 0.0141* |
| CD6 | 0.7502 | 0.0019** | 0.0075* |
| CD3E (OKT3) | 0.8849 | 0.0043** | 0.0032** |

In contrast to PSI alone, combining product PSI or CD4+ PSI with CAR peak levels, respectively, was significantly associated with grade 3+NT (FIGS. 9A-9F). CD4+ and CD8+ PSIs were calculated for each product by applying the same pre-specified formula to the two product T cell subsets separately. FIGS. 9A-9F show the association between PSI in conjunction with CAR T cell levels in blood and grade 3+ neurologic toxicity (NT; FIGS. 9A-9F). FIGS. 10A-10F show the association between PSI in conjunction with CAR T cell levels in blood, and cytokine release syndrome (CRS; FIG. 10A-10F). CAR T cell levels in blood were measured by qPCR and correlated with grade 3+ adverse events. A composite index integrating PSI and CAR T cell expansion in vivo was developed and associated with neurologic events (NE) or CRS, respectively. Whole-product PSI, CD4+ PSI, and IL-17A PSI indexes were all evaluated in conjunction with CAR peak levels. The 2 metrics were combined into a joint metric to test their association with a patient outcome. The metrics were added to each other after first standardizing each of them to have unit variance. This standardization was achieved by dividing the metric by their respective standard deviation to bring them to a common magnitude/scale. Statistical values were computed using the Mann Whitney U test. P values were not adjusted for multiplicity.

To determine whether subsets of polyfunctional T cells producing cytokines such as IL-17A were associated with grade 3+NT, a cytokine-specific PSI was computed by multiplying the percentage of polyfunctional T cells secreting a given cytokine with the average signal intensity for that cytokine. These cytokine PSI values were analyzed in relation to outcome. IL-17A PSI, defined post-hoc, plus CAR peak cell levels, had a significant association with grade 3+NT (P=0.0007; FIGS. 9A-9F). Individually, CAR peak cell levels and IL-17A PSI were associated with grade 3+NT (P=0.0015 and P=0.0574, respectively). IL-17A PSI correlated strongly with the percentage of Th17 cells measured by epigenetic marking and IL-17A production in product co-culture (P<0.0001 for both comparisons), and associated with the CD4/CD8 ratio, percentage of T helper (Th) cells, and IL-6 levels in product co-culture (Table 3). Grade 3+ CRS was associated with the global product PSI plus CAR peak levels (FIGS. 10A-10F).

Association between major product characteristics and IL-17A PSI was performed by linear regression. CD4:CD8 ratio was calculated based on flow cytometry measurements; % T helper and % Th17 cells were measured based on epigenetic analysis; IL-17A and IL-6 in co-culture of product and target cells were measured by ELISA; and IL-17A PSI was computed as described herein. * P<0.05.  P<0.005. * P<0.0005.

TABLE 3

Associations between product IL-17 PSI and product T cell characteristics.

| Product characteristics | PSI | IL-17A PSI |
| --- | --- | --- |
| CD4:CD8 ratio | 0.2008 | 0.0008** |
| % T Helper (epigenetic) | 0.7074 | 0.0038** |
| % Th17 (epigenetic) | 0.7407 | <0.0001*** |
| IL-17A in co-culture | 0.3129 | <0.0001*** |
| IL-6 in co-culture | 0.0864 | 0.0006** |

Figure 5D:
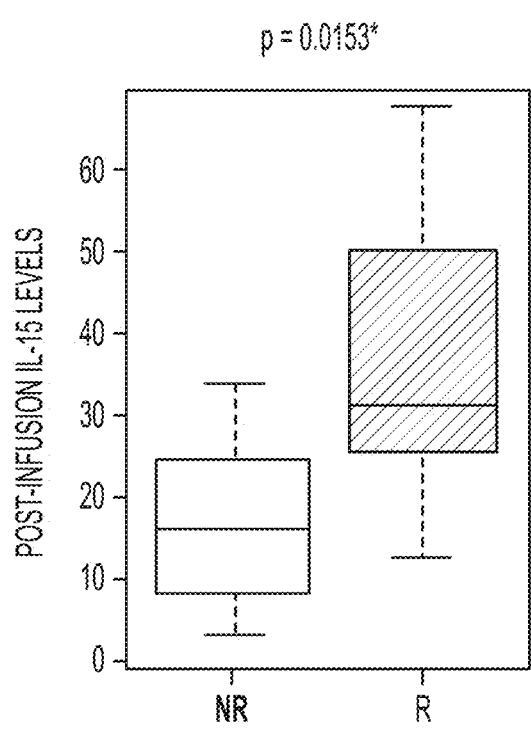
Figure 5E:
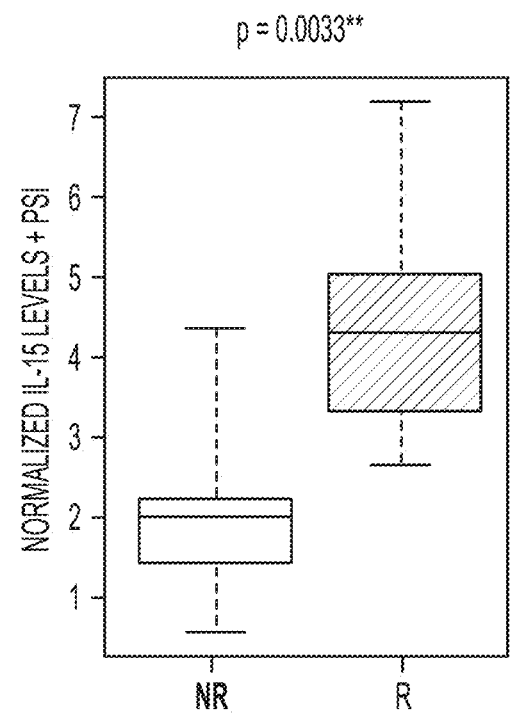

PSI in conjunction with CAR T cell expansion in vivo or in conjunction with conditioning-driven IL-15 pre-CAR T cell infusion correlates with objective response (OR) (FIGS. 5A-5D). Product PSI combined with IL-15 levels at day 0 had a statistically significant association with OR (P=0.0033) (FIG. 5E). Objective response also was associated with PSI (P=0.0119) (FIG. 5A) and IL-15 (P=0.0153) (FIG. 5D). However, PSI and IL-15 on day 0 did not have a statistically significant association with each other. In addition, IL-15 on day 0 in conjunction with CD4+ PSI, or with IL-17A PSI, were also strongly associated with OR (P<0.0004; FIGS. 7A and 7B). Day 0 levels of IL-15+IL-17A PSI were also associated with grade 3+NT (FIGS. 11A-F) and CRS (FIGS. 12A-12F). Product PSI together with CAR T cell expansion, or pre-CAR T cell infusion levels of IL-15, contribute jointly to clinical outcomes after CAR T cell therapy. These findings also point to the prominent role of IL-17A polyfunctional T cells in clinical outcomes, particularly NT, associated with CAR T cell therapy.

Association between PSI in conjunction with pretreatment IL-15 levels in blood, and grade 3+NE (FIGS. 11A-11F) or CRS (FIGS. 12A-12F). IL-15 levels in blood were measured by ELISA and correlated with grade 3+ AEs. A composite index integrating PSI and IL-15 levels associated with grade 3+NE or CRS, respectively. Whole-product PSI, CD4+ PSI, and IL-17A PSI were all evaluated in conjunction with IL-15 levels. Statistical values were computed using the Mann Whitney U test. P values were not adjusted for multiplicity.

What is claimed:

1. A method of treating a malignancy in a patient comprising:
   (a) obtaining a plurality of T cells comprising one or more chimeric antigen receptors; and
   (b) administering an effective dose of the T cells comprising a pre-determined amount of polyfunctional T cells determined using the Polyfunctional Strength Index (PSI) to the patient, wherein the PSI incorporates protein intensities and percentage of polyfunctional cells expressing those proteins, wherein the polyfunctional cells comprise CD4+T cells that have been determined to secrete IL-17alpha, IL-8, and/or IFNgamma and/or CD8+T cells that have been determined to secrete Granzyme B, IFNgamma, IL-8, and/or MIP-1alpha, when stimulated with the antigen.

2. The method of claim 1, wherein the PSI is calculated by multiplying the percentage of polyfunctional cells by the sum of the mean fluorescence intensity of the proteins secreted by the polyfunctional cells.

3. The method of claim 1, wherein the PSI is obtained by a method comprising (i) determining a desired percentage of Polyfunctional T cells; and (ii) obtaining a pre-determined cytokine profile.

4. The method of claim 1, wherein the effective dose is adjusted proportionally with tumor burden.

5. The method of claim 1, wherein the pre-determined amount of polyfunctional T cells is determined using a composite index comprising at least two metrics.

6. The method of claim 1, wherein the chimeric antigen receptor targets a tumor antigen.

7. The method of claim 1, wherein the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia (BALL), T-cell acute lymphoid leukemia (TALL), acute lymphoid leukemia (ALL), chronic myelogenous leukemia (CML), B cell prolymphocytic leukemia, blastic plasmacytoid dendritic cell neoplasm, Burkitt's lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, asymptomatic myeloma (smoldering multiple myeloma or indolent myeloma) and other plasma cell proliferative disorders, monoclonal gammapathy of undetermined significance (MGUS), plasma cell dyscrasia, solitary myeloma, solitary plasmacytoma, extramedullary plasmacytoma, and multiple plasmacytoma and other plasmacytomas, systemic amyloid light chain amyloidosis, POEMS syndrome (also known as Crow-Fukase syndrome, Takatsuki disease, and PEP syndrome), metastatic melanoma, high grade B-cell lymphoma or a combination thereof.

8. The method of claim 1 further comprising modulating the effective dose to adjust the total number of polyfunctional cells.

9. The method of claim 1 further comprising modulating the effective dose to adjust the total PSI.

10. The method of claim 1, further comprising: measuring the Polyfunctional Strength Index (PSI) of the T cells; and preparing an effective dose comprising a predetermined amount of polyfunctional T cells.

11. The method of claim 1, further comprising: determining the amount of polyfunctional T cells in the plurality of T cells; and determining if the patient will respond to chimeric antigen receptor treatment based on the amount of polyfunctional T cells.

12. The method of claim 1, further comprising preparing an effective dose comprising a predetermined amount of polyfunctional T cells.

13. The method of claim 6, wherein the tumor associated antigen is a tumor-associated surface antigen selected from 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-I, intestinal carboxyl esterase, kappa chain, LAGA-la, lambda chain, Lassa Virus-specific antigen, lectin-reactive AFP, CD3, MAGE, MAGE-Al and all other lineage-specific or tissue specific antigens, major histocompatibility complex (MHC) molecule, major histocompatibility complex (MHC) molecule presenting a tumor-specific peptide epitope, M-CSF, melanoma-associated antigen, mesothelin, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the Al domain of tenascin-C(TnC Al), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers.

14. The method of claim 1, wherein the polyfunctional cells comprise CD4+T cells that have been determined to secrete IL-17alpha, IL-8, and/or IFNgamma and CD8+T cells that have been determined to secrete Granzyme B, IFNgamma, IL-8, and/or MIP-1alpha, when stimulated with the antigen.

15. The method of claim 1, wherein the polyfunctional cells comprise CD4+T cells that have been determined to secrete IL-17alpha, IL-8, and IFNgamma and CD8+T cells that have been determined to secrete Granzyme B, IFNgamma, IL-8, and/or MIP-1alpha, when stimulated with the antigen.

16. The method of claim 1, wherein the polyfunctional cells comprise CD4+T cells that have been determined to secrete IL-17alpha, IL-8, and IFNgamma and CD8+T cells that have been determined to secrete Granzyme B, IFNgamma, IL-8, and MIP-1alpha, when stimulated with the antigen.

* * * * *